US012655144B2

(12) United States Patent
Nishikawa et al.

(10) Patent No.: US 12,655,144 B2
(45) Date of Patent: Jun. 16, 2026

(54) METHOD FOR PRODUCING HETEROCYCLIC COMPOUND

(71) Applicant: TAKEDA PHARMACEUTICAL COMPANY LIMITED, Osaka (JP)

(72) Inventors: Hitoaki Nishikawa, Fujisawa (JP); Naohiro Taya, Fujisawa (JP); Hiroshi Banno, Fujisawa (JP); Masatoshi Yamada, Osaka (JP); Kazuki Azuma, Osaka (JP); Ayaka Suzuki, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 744 days.

(21) Appl. No.: 17/927,584

(22) PCT Filed: May 26, 2021

(86) PCT No.: PCT/JP2021/019911
§ 371 (c)(1),
(2) Date: Nov. 23, 2022

(87) PCT Pub. No.: WO2021/241611
PCT Pub. Date: Dec. 2, 2021

(65) Prior Publication Data

US 2023/0192685 A1 Jun. 22, 2023

(30) Foreign Application Priority Data

May 27, 2020 (JP) ................................ 2020-092687

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS

2021/0332045 A1 10/2021 Hirayama et al.
2022/0048916 A1* 2/2022 Hirayama ............ A61K 9/4858
2022/0089595 A1 3/2022 Hirayama et al.

FOREIGN PATENT DOCUMENTS

WO WO-2018141749 A1 * 8/2018 ............ A61K 31/50
WO 2020/111087 A1 6/2020

* cited by examiner

*Primary Examiner* — Andrew D Kosar
*Assistant Examiner* — Phillip Matthew Rzeczycki
(74) *Attorney, Agent, or Firm* — Sughrue Mion, PLLC

(57) ABSTRACT

A method for producing a compound represented by the formula (X):

(X)

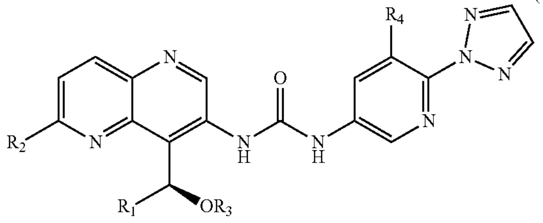

or a salt thereof and has a MALT1 inhibitory action, the said method containing a step for producing a compound a compound represented by the formula (B-2):

(B-2)

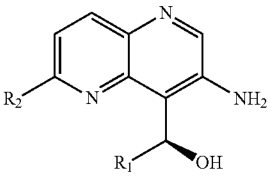

or a salt thereof and being characterized by comprising crystallizing a salt of a compound represented by the formula (B-1):

(B-1)

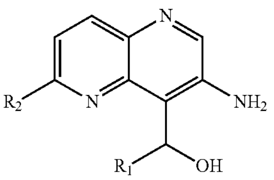

and an optically active organic acid.
(In the formulae, each symbol is as defined in the specification.)

10 Claims, No Drawings

Specification includes a Sequence Listing.

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Synthetic sequence

<400> SEQUENCE: 1

ggaagtggct caggtagc                                               18
```

METHOD FOR PRODUCING HETEROCYCLIC COMPOUND

CROSS REFERENCE TO RELATED APPLICATIONS

This application is a National Stage of International Application No. PCT/JP2021/019911 filed May 26, 2021, claiming priority based on Japanese Patent Application No. 2020-092687 filed May 27, 2020.

TECHNICAL FIELD

The present invention relates to a method for producing efficiently a novel heterocyclic compound that have an effect of inhibiting MALT1 (Mucosa associated lymphoid tissue protein 1) and is expected as useful as a prophylactic or therapeutic drug for cancer etc.

BACKGROUND ART

An inhibitor that inhibits the activity of MALT1 is expected to be able to correct the enhancement of the activity of MALT1 caused by abnormalities in T-cell receptor signal and B-cell receptor signal, and is considered to be useful as a prophylactic or therapeutic drug for cancer, inflammatory disease and the like caused by the activity of MALT1.

Conventionally, research about a MALT1 inhibitor has been promoted in the relevant technical field. For example, Patent Literature 1 discloses the compounds having an effect of inhibiting MALT1 and being useful for treating autoimmune disorders and inflammatory diseases such as rheumatoid arthritis, multiple sclerosis, systemic lupus erythematosus and vasculitis conditions, cancers derived from the haemopoietic system, including chronic myelogenous leukemia, myelogenous leukemia, non-Hodgkin's lymphoma and other B-cell lymphomas, or solid tumors and the like, and Patent Literature 2 discloses the compounds having an effect of inhibiting MALT1 and being useful for treating autoimmune disorders and inflammatory diseases such as rheumatoid arthritis, multiple sclerosis, psoriasis, Sjogren's syndrome, systemic lupus erythematosus and vasculitis conditions, cancers derived from the haemopoietic system, including chronic myelogenous leukemia, myelogenous leukemia, non-Hodgkin's lymphoma and other B-cell lymphomas, or solid tumors and the like. Patent Literature 3, 4, and 5 disclose the compounds having an effect of inhibiting MALT1.

CITATION LIST

Patent Literatures

Patent Literature 1: WO 2015/181747
Patent Literature 2: WO 2017/081641
Patent Literature 3: WO 2018/020474
Patent Literature 4: WO 2018/085247
Patent Literature 5: WO 2021/000855

SUMMARY OF INVENTION

Technical Problem

In these situations, it has been found that the novel compound represented by the following formula (X) or a salt thereof can have an excellent effect of inhibiting MALT1 (International Application Number: PCT/JP2019/046261 (International Filing Date: 27 Nov. 2019); International Publication Number: WO2020/111087 (International Publication Date Apr. 6, 2020).

(X)

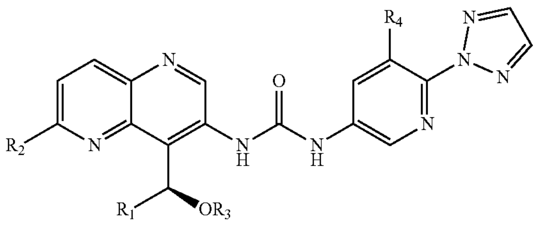

(wherein $R_1$ represents a methyl group;

$R_2$ represents 1) a $C_{1-6}$ alkyl group or 2) a halogen atom;

$R_3$ represents a $C_{1-6}$ alkyl group;

$R_4$ represents a $C_{1-6}$ alkyl group which may be substituted with halogen atoms.)

More specifically, the novel compound represented by the following formula (X1) or (X2) has been founded (occasionally abbreviated as the compound (X1) or the compound (X2) in the following description).

(X1)

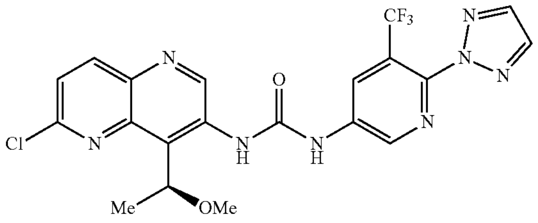

Chemical name: (S)—N-(6-Chloro-4-(1-methoxyethyl)-1,5-naphthyridine-3-yl)-N'-(6-(2H-1,2,3-triazole-2-yl)-5-(trifluoromethyl)pyridine-3-yl)urea (Compound of example 2 in the above International Application)

(X2)

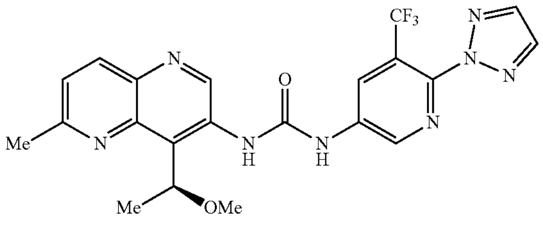

Chemical name: (S)—N-(4-(1-methoxyethyl)-6-methyl-1,5-naphthyridine-3-yl)-N'-(6-(2H-1,2,3-triazole-2-yl)-5-(trifluoromethyl) pyridine-3-yl)urea (Compound of example 3 in the above International Application)

A detailed description is made of an excellent MALT1 inhibitory activity and a production method of the compound (X1) or (X2) in the page of [example] described later. To describe it briefly, these compounds are produced in the following synthetic scheme.

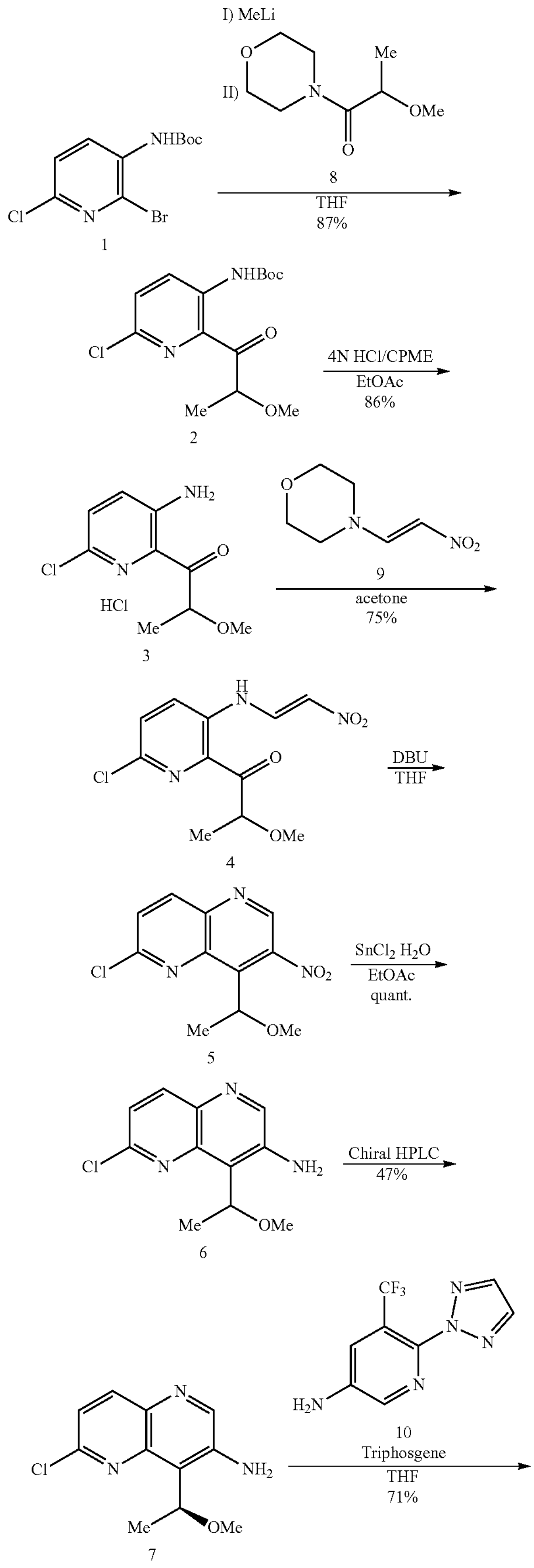
-continued
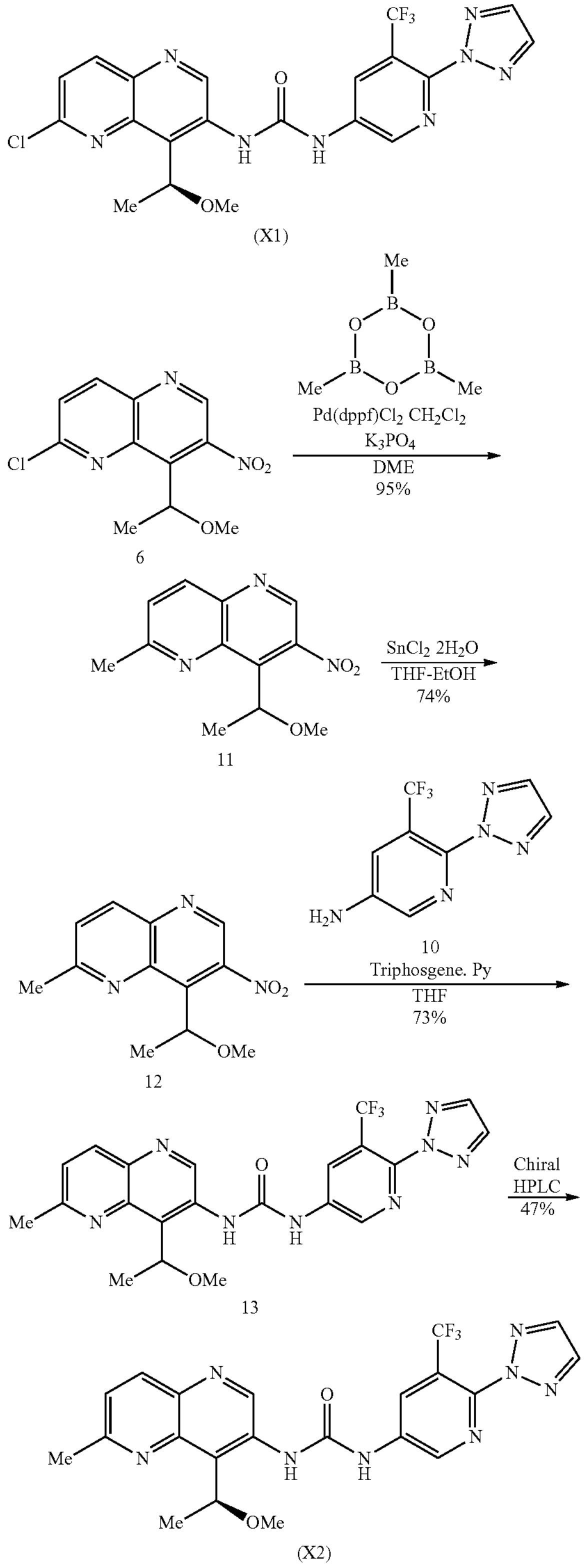
In order to produce compound (X1) or (X2) with high optical purity, purification by chiral column is used in the producing process or in the final process. However, chiral column purification is complicated and is not suitable for large-scale synthesis of compounds with high optical purity.

Therefore, the above synthetic scheme is not always sufficient as a method for industrially producing a compound (X) with high optical purity, and there is a need to create a producing method more suitable for industrially producing the compound (X).

Solution to Problem

As a result of diligent studies to solve the above problems, it was found that the highly optically pure compound (B-2) could be efficiently produced by the optical resolution method using the formation of diastereomer salts of compound (B-1) with optically active organic acids instead of the chiral column purification. Further, improvements were made in conjunction with the synthetic scheme leading to compound 7, such as the preparation of compound (B-1) by asymmetric reduction of compound (A), and a novel preparation method suitable for the industrial production of compound (X) and a novel intermediate were found, thereby completing the present invention. The present invention enables efficient production of a novel compound (X) which have an excellent effect of inhibiting MALT1 and is expected to be developed and launched as a drug in the future.

The producing method of the present invention is represented by the following synthetic scheme.

Scheme (A)

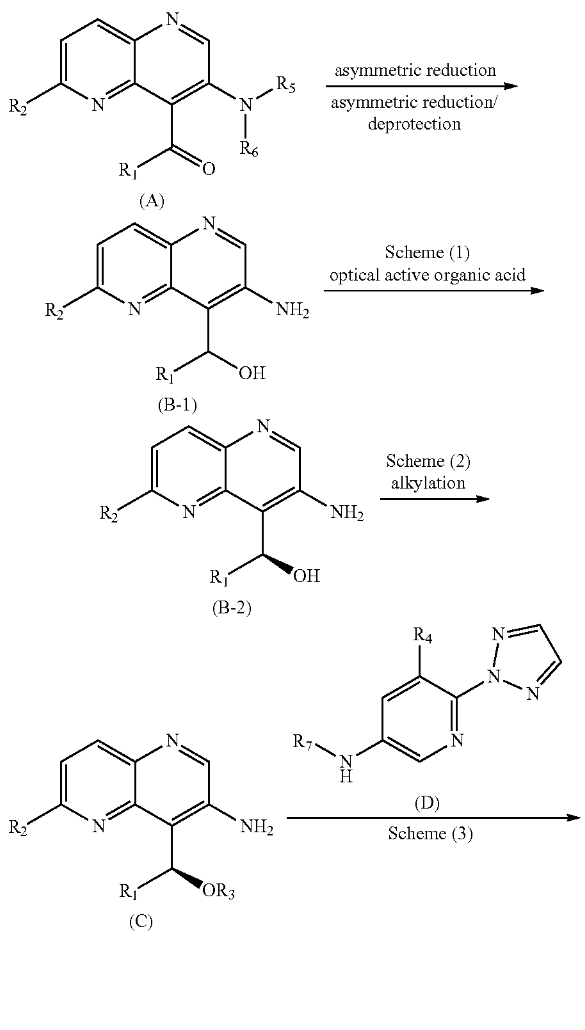

(A)

(B-1)

(B-2)

(D)

(C)

-continued

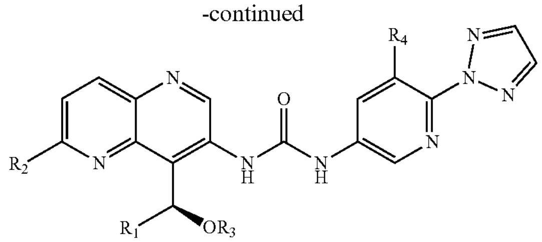

(X)

wherein $R_1$-$R_4$ respectively represent the same meanings as above;

$R_5$ and $R_6$ respectively and independently represent a hydrogen atom or an amino protecting group; and $R_7$ respectively represents a hydrogen atom, a $C_{1-6}$ alkoxy group which may be substituted halogen atoms, an aryloxycarbonyl group which may be substituted nitro groups.

Although each of the above steps is important as constituting a producing method of the present invention, among them, step (1), which is characterized by crystallization of a diastereomeric salt of a compound represented by the formula (B-1) (Hereinafter, compound (B-1) may be abbreviated. The same applies to compounds represented by other formulae.) and an optically active organic acid, is a producing step of the compound (B-2), and is a core step of the present invention. The compound (B-2) with a high optical purity can be obtained by this step, and the compound (X) or a salt thereof which is an excellent MALT1 inhibitor can be produced by carrying out the subsequent steps (2) and (3) using the obtained compound (B-2) or a salt thereof. Accordingly, a method for producing compound (X) or a salt thereof, which includes carrying out step (1), is one preferred embodiment of the present invention.

The compound (C) or a salt thereof obtained in step (2) is a novel compound. Therefore, the present invention is also useful as a method for producing a new compound (C) useful for producing the compound (X).

The compound (B-1) used as a starting material in the step (1) may be a racemate, or an optically active substance which is a mixture containing one optical isomer in a larger amount than the other optical isomer. The compound (B-1) which is the "optically active substance" can be obtained by subjecting the compound (A) to asymmetric reduction (step (A)). Therefore, the step (A) is another core step of the present invention. A method for producing compound (X) or a salt thereof comprising performing step (A) in combination with step (1) is another preferred embodiment of the present invention.

Although not limited, a preferred embodiment of the present invention is shown below.

[1] A method for producing a compound represented by the formula (B-2):

(B-2)

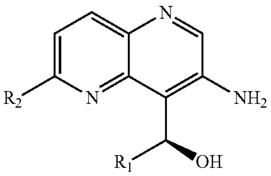

(wherein $R_1$ represents a methyl group and $R_2$ represents a $C_{1-6}$ alkyl group or a halogen atom.) (compound (B-2)) or a salt thereof, comprising crystallizing a salt of a compound represented by the formula (B-1):

(B-1)

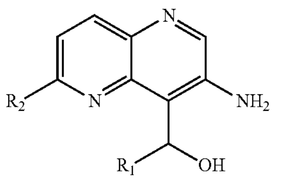

(wherein $R_1$ and $R_2$ respectively represent the same meanings as above.) (compound (B-1)) and an optically active organic acid.

[2] A method for producing a compound represented by the formula (C):

(C)

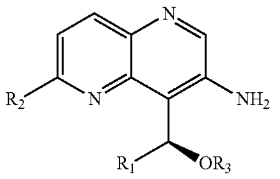

(wherein $R_1$ represents a methyl group, $R_2$ represents a $C_{1-6}$ alkyl group or a halogen atom and $R_3$ represents a $C_{1-6}$ alkyl group.) (compound (C)) or a salt thereof, comprising 1) crystallizing a salt of the compound represented by the formula (B-1):

(B-1)

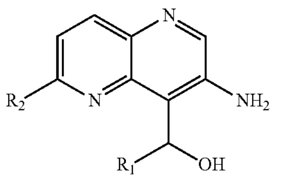

(wherein $R_1$ and $R_2$ respectively represent the same meanings as above.) and an optically active organic acid to obtain the compound represented by the formula (B-2):

(B-2)

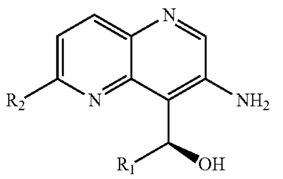

(wherein $R_1$ and $R_2$ respectively represent the same meanings as above.) or a salt thereof, and 2) subjecting the obtained compound (B-2) or a salt thereof to an alkylation reaction.

[3] A method for producing a compound represented by the formula (X):

(X)

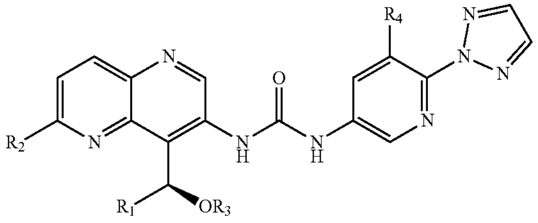

(wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted halogen atoms.) (compound (X)) or a salt thereof, comprising 1) crystallizing a salt of the compound represented by the formula (B-1):

(B-1)

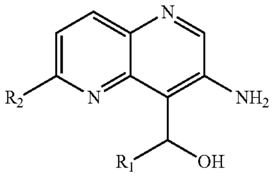

(wherein $R_1$ and $R_2$ respectively represent the same meanings as above.) and an optically active organic acid to obtain the compound represented by the formula (B-2):

(B-2)

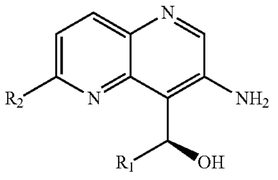

(wherein $R_1$ and $R_2$ respectively represent the same meanings as above.) or a salt thereof, 2) subjecting the obtained compound (B-2) or a salt thereof to an alkylation reaction to obtain the compound represented by the formula (C):

(C)

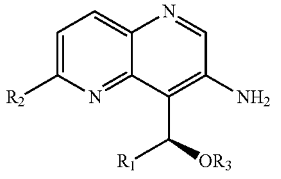

(wherein $R_1$ to $R_3$ respectively represent the same meanings as above.) or a salt thereof, and 3) subjecting the obtained compound (C) or a salt thereof to a reaction with compound represented by the formula (D):

(D)

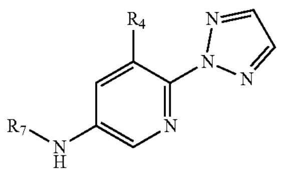

(wherein $R_4$ represents the same meanings as above, and $R_7$ represents a hydrogen atom, a $C_{1-6}$ alkoxy group which may be substituted halogen atoms, or an aryloxycarbonyl group which may be substituted nitro groups.) (compound (D)) or a salt thereof.

[4] A method for producing a compound represented by the formula (B-2):

(B-2)

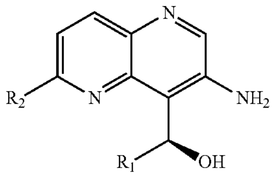

(wherein $R_1$ represents a methyl group and $R_2$ represents a $C_{1-6}$ alkyl group or a halogen atom) or a salt thereof, comprising 1) subjecting the compound represented by the formula (A):

(A)

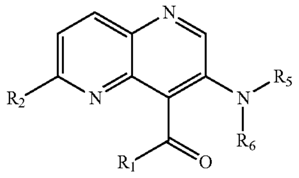

(wherein $R_1$ and $R_2$ respectively represent the same meanings as above, $R_5$ and $R_6$ respectively and independently represent a hydrogen atom or an amino protecting group.) (compound (A)) or a salt thereof 1) to an asymmetric reduction reaction of a carbonyl group, or 2) to an asymmetric reduction reaction of a carbonyl group and a deprotection reaction of an amino protecting group to obtain the compound represented by the formula (B-1):

(B-1)

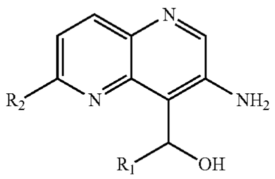

(wherein $R_1$ and $R_2$ respectively represent the same meanings as above.) or a salt thereof, and 2) crystallizing a salt of the obtained compound (B-1) and an optically active organic acid.

[5] A method for producing a compound represented by the formula (X):

(X)

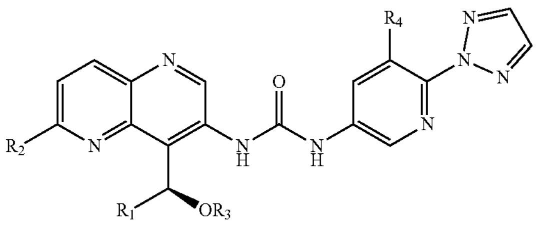

(wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted halogen atoms) or a salt thereof, comprising 1) subjecting the compound represented by the formula (A):

(A)

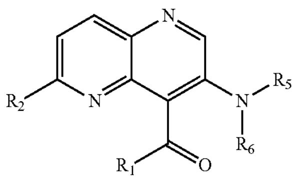

(wherein $R_1$ and $R_2$ respectively represent the same meanings as above, $R_5$ and $R_6$ respectively and independently represent a hydrogen atom or an amino protecting group.) or a salt thereof 1) to an asymmetric reduction reaction of carbonyl group, or 2) to an asymmetric reduction reaction of carbonyl group and a deprotection reaction of an amino protecting group to obtain the compound represented by the formula (B-1):

(B-1)

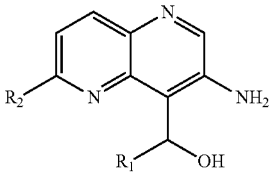

(wherein $R_1$ and $R_2$ respectively represent the same meanings as above.) or a salt thereof, 2) crystallizing a salt of the obtained compound (B-1) and an optically active organic acid to obtain the compound represented by the formula (B-2):

(B-2)

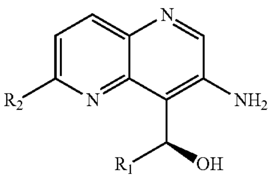

(wherein $R_1$ and $R_2$ respectively represent the same meanings as above.) or a salt thereof, 3) subjecting the obtained compound (B-2) or a salt thereof to an alkylation reaction to obtain the compound represented by the formula (C):

(C)

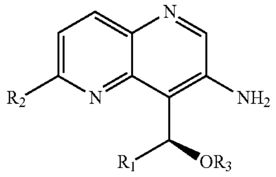

(wherein $R_1$ to $R_3$ respectively represent the same meanings as above.) or a salt thereof, and 4) subjecting the obtained compound (C) or a salt thereof to a reaction with compound represented by the formula (D) (compound (D))

(D)

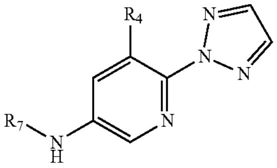

(wherein $R_4$ represents the same meanings as above, and $R_7$ represents a hydrogen atom, a $C_{1-6}$ alkoxy group which may be substituted halogen atoms, or an aryloxycarbonyl group which may be substituted nitro groups.) or a salt thereof.

[6] The method for producing according to any one of [1] to [5], wherein the optically active organic acid is selected from D-(−)-tartaric acid, L-(+)-tartaric acid, (S)-(−)-2-pyridone-5-carboxylic acid, (R)-(+)-2-pyridone-5-carboxylic acid, L-malic acid, D-malic acid, (S)-(+)-camphor-10-sulfonic acid, (R)-(−)-camphor-10-sulfonic acid, (S)-(+)-2-(6-methoxy-2-naphthyl) propionic acid, (R)-(−)-2-(6-methoxy-2-naphthyl)propionic acid, (+)-cis-2 benzamidocyclohexanecarboxylic acid, (−)-cis-2 benzamidocyclohexanecarboxylic acid, dehydroabietic acid, (R)-(N-(3,5-dinitrobenzoyl)-α-phenylglycine, (S)-(+)-N-(3,5-dinitrobenzoyl)-α-phenylglycine, D-(−)-quinic acid and L-(+)-quinic acid.

[7] The method for producing a compound according to any one of [1] to [5], wherein the optically active organic acid is D-(−)-tartaric acid.

[8] A method for producing a compound represented by the formula (X):

(X)

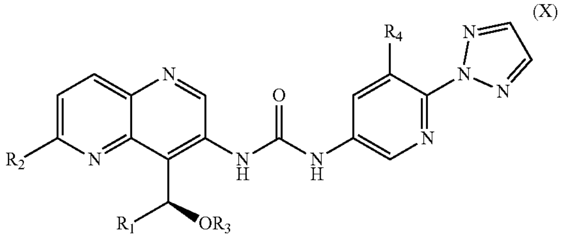

(wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted halogen atoms) or a salt thereof comprising subjecting the compound represented by the formula (C):

(C)

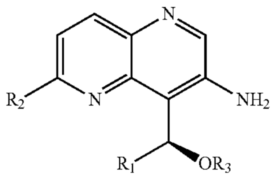

(wherein $R_1$ to $R_3$ respectively represent the same meanings as above.) or a salt thereof to a reaction with compound represented by the formula (D):

(D)

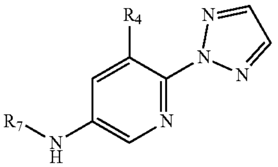

(wherein $R_4$ represents the same meanings as above, and $R_7$ represents a hydrogen atom, a $C_{1-6}$ alkoxy group which may be substituted halogen atoms, or an aryloxycarbonyl group which may be substituted nitro groups.) or a salt thereof.

[9] A method for producing a compound represented by the formula (X):

(X)

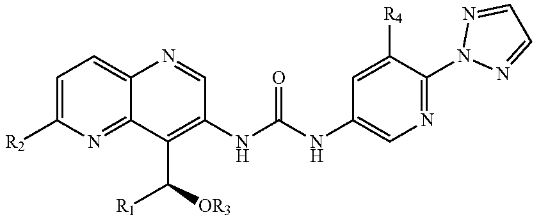

(wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted halogen atoms) (compound (X)) or a salt thereof comprising 1) subjecting compound represented by the formula (B-2):

(B-2)

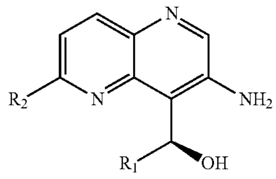

(wherein $R_1$ and $R_2$ respectively represent the same meanings as above.) or a salt thereof, or a salt thereof (compound (B-2)) to an alkylation reaction to obtain the compound represented by the formula (C):

(C)

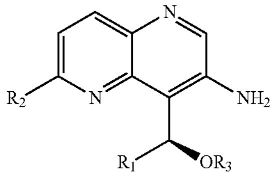

(wherein $R_1$ to $R_3$ respectively represent the same meanings as above.) (compound (C)) or a salt thereof, 2) subjecting the obtained compound (C) or a salt thereof to a reaction with compound represented by the formula (D):

(D)

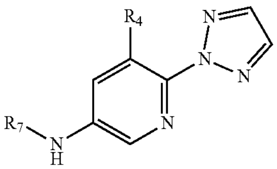

(wherein $R_4$ represents the same meanings as above, and $R_7$, represents a hydrogen atom, a $C_{1-6}$ alkoxy group which may be substituted halogen atoms, or an aryloxycarbonyl group which may be substituted nitro groups.) (compound (D)) or a salt thereof.

[10] A compound represented by the formula (C) or a salt thereof.

(C)

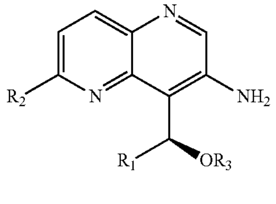

(wherein $R_1$-$R_3$ respectively represent the same meanings as above.)

Advantageous Effects of Invention

The present invention provides an industrial production method for efficiently synthesizing a compound (X) or a salt thereof, which is a novel MALT1 inhibitor having a high optical purity, in a large amount with a shorter number of steps, without the need for complicated operations such as chiral column purification.

DESCRIPTION OF EMBODIMENT

The salt of the compound (X) is preferably a pharmacologically acceptable salt. Examples of such a salt include salts with inorganic acids, salts with organic acids, and salts with acidic amino acids.

Suitable examples of the salts with inorganic acids include salts with hydrochloric acid, hydrobromic acid, nitric acid, sulfuric acid and phosphoric acid.

Suitable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.

Suitable examples of the salts with acidic amino acids include salts with aspartic acid and glutamic acid.

Hereinafter, a detailed description is made of the definition of each substituent used in the description. Unless otherwise specified, each substituent has the following definition.

In the description, examples of the "halogen atom" include fluorine, chlorine, bromine and iodine.

In the description, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the description, examples of the "$C_{1-6}$ alkyl group which may be substituted halogen atoms" include a $C_{1-6}$ alkyl group which may have 1 to 7 halogen atoms, preferably 1 to 5 halogen atoms. Examples include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl.

In the description, examples of "aryloxycarbonyl group" include a $C_{6-14}$aryloxy-carbonyl group such as phenyloxycarbonyl, 1-naphthyloxycarbonyl, 2-naphthyloxycarbonyl. The aryl moiety of the "aryloxycarbonyl group" may have 1 to 3 nitro groups.

In the description, examples of "amino protecting group" include amino protecting groups commonly used in the art, and examples thereof may include a $C_{1-6}$alkoxy-carbonyl group (e.g., tert-butoxycarbonyl) as preferred.

In the description, unless otherwise specified, the formula, chemical structure, or compound name given without specifying stereochemistry means a mixture of possible isomers (including equal mixtures).

The above-mentioned compound (B-1) is taken as an example.

(B-1)

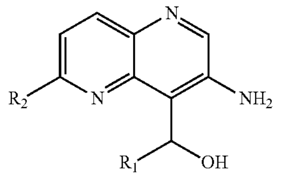

The compound (B-1) means a mixture of two optical isomers represented by the following formula.

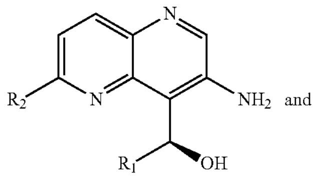

and

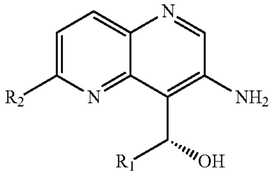

The method for producing a compound of the present invention will be described below. The raw materials and reagents used in each step of the following producing methods and the obtained compounds may form salts. Such a salt is not particularly limited as long as the reaction proceeds, but examples thereof may include those similar to the salt of the compound (X) (e.g., a salt with an inorganic acid).

When the compound obtained in each step is a free compound, it can be converted to the desired salt by a method which is known in itself. On the other hand, when the compound obtained in each step is a salt, the compound can be converted into a free body or another salt of the desired type by a method known in itself. Such a salt is not particularly limited as long as the reaction proceeds, but examples thereof may include those similar to the salt of the compound (X) (e.g., a salt with an inorganic acid). Such conversion of the salt can be performed for the purpose of improving the operability of the reaction, improving the efficiency of the reaction, etc. Further, such conversion can be performed at a step before the reaction in each step. If necessary, it can be reconverted to a free body.

The compound obtained in each step can be used in the subsequent reaction as a reaction solution or as a crude product. Further, the compound obtained in each step can be isolated and purified from the reaction mixture by separation means such as concentration, crystallization, recrystallization, distillation, solvent extraction, fractionation, and chromatography according to the usual method.

Commercially available raw materials and reagents may be used as they are if they are commercially available.

Unless otherwise specified, these reactions may be performed to be dissolved or be suspended without solvent or in an appropriate solvent. Examples of such solvents include those described in the examples that follow, and the following.

Alcohols: methanol, ethanol, tert-butyl alcohol, 2-methoxyethanol, 1-propanol, 2-propanol, t-amyl alcohol, etc.;

Ethers: diethyl ether, diisopropyl ether, cyclopentyl methyl ether, diphenyl ether, tetrahydrofuran, 1,2-dimethoxyethane, 1,4-dioxane, etc.;

Aromatic hydrocarbons: chlorobenzene, toluene, xylene, etc.;

Saturated hydrocarbons: cyclohexane, hexane, etc.;

Amides: N, N-dimethylformamide, N, N-dimethylacetamide, N-methylpyrrolidone, etc.;

Halogenated hydrocarbons: dichloromethane, carbon tetrachloride, etc.;

Nitriles: acetonitrile, etc.;

Sulfoxides: dimethyl sulfoxide, etc.;

Organic bases: pyridine, triethylamine, etc.;

Acid anhydrides: acetic anhydride, etc.;

Organic acids: formic acid, acetic acid, trifluoroacetic acid, etc.;

Inorganic acids: hydrochloric acid, sulfuric acid, etc.;

Esters: ethyl acetate, isopropyl acetate, etc.;

Ketones: acetone, methyl ethyl ketone, etc.;

Water.

The above solvents may be used by mixing two or more kinds at an appropriate ratio.

Hereinafter, each step of the present invention will be described in detail in accordance with an embodiment of the present invention.

An Embodiment [1]

An embodiment [1] of the present invention is a method for producing the compound (B-2) or a salt thereof having a high optical purity by optical resolution including crystallization of a salt of the compound (B-1) and an optically active organic acid (step (1)).

The optical resolution is performed by mixing the compound (B-1) with an optically active organic acid in a solvent and collecting the precipitated crystal by filtration. When the compound (B-1) forms a salt in the step (1), the salt is converted to a free body (compound (B-1)) by using a base, and then mixed with an optically active organic acid.

The "optically active organic acid" used in the step (1) refers to an optically active organic acid of high optical purity substantially (e.g., optical purity ≥95%) consisting of only one optical isomer, and commercially available products may be used when available.

The optically active organic acids used in the step (1) are, for example, D-(−)-tartaric acid, L-(+)-tartaric acid, (S)-(−)-2-pyridone-5-carboxylic acid, (R)-(+)-2-pyridone-5-carboxylic acid, L-malic acid, D-malic acid, (S)-(+)-camphor-10-sulfonic acid, (R)-(−)-camphor-10-sulfonic acid, (S)-(+)-2-(6-methoxy-2-naphthyl)propionic acid, (R)-(−)-2-(6-methoxy-2-naphthyl)propionic acid, (+)-cis-2 benzamidocyclohexanecarboxylic acid, (−)-cis-2-benzamidocyclohexanecarboxylic acid, dehydroabietic acid, (R)-(−)-N-(3,5-dinitrobenzoyl)-α-phenylglycine, (S)-(+)-N-(3,5-dinitrobenzoyl)-α-phenylglycine, D-(−)-quinic acid, and L-(+)-quinic acid, etc.

While the step (1) can be performed by selecting an optically active organic acid as appropriate by a person skilled in the art, the followings are preferred: D-(−)-tartaric acid, (R)-(−)-camphor-10-sulfonic acid, and (R)-(−)-N-(3,5-dinitrobenzoyl)-α-phenylglycine, and particularly preferred one includes D-(−)-tartaric acid.

The amount of the optically active organic acid to be used is usually 0.3 to 1.2 mol, and preferably 0.4 to 1.0 mol per mol of the compound (B-1).

Solvents for mixing with optically active organic acids include esters, nitriles, alcohols, ethers, aromatic hydrocarbons, saturated hydrocarbons, amides, halogenated hydrocarbons, water, and the like.

The mixing is generally performed at 0 to 100° C., preferably 25 to 60° C.

The reaction time is generally from about 10 minutes to about 96 hours, and preferably from about 0.5 hours to about 80 hours.

In the step (1), the compound (B-1) to be used as a raw material may be a racemate or a mixture ("optically active substance") containing one optical isomer in a larger amount than the other optical isomer.

The compound (B-1) which is the "optically active substance" can be obtained, for example, by subjecting the compound (A) to asymmetric reduction (Step (A)), or the "optically active substance" can be obtained by a person skilled in the art according to other appropriate methods. In the step, the "optically active substance" is, for example, without limitation, preferably a substance containing 70 to 99% (molar ratio) of the objective optical isomer (optical isomer represented by formula (B-2)), more preferably a substance containing 80 to 99% (molar ratio), and most preferably a substance containing 85 to 98% (molar ratio).

An Embodiment [2]

An embodiment [2] of the present invention is a method for continuously performing Step (1) and Step (2), which is a producing method characterized by obtaining the compound (B-2) or a salt thereof with high optical purity by optical resolution characterized by crystallizing a salt of the compound (B-1) and an optically active organic acid (Step (1)), and obtaining the compound (C) or a salt thereof by subjecting the obtained compound (B-2) or a salt thereof to an alkylation reaction (Step (2)).

(1) Step (1)

In this embodiment, the step (1) can be performed according to the method described in the above-mentioned embodiment [1].

(2) Step (2)

In Step (2), the reaction is performed by subjecting the compound (B-2) or a salt thereof to reaction with an alkylating agent in a solvent.

Examples of the alkylating agent may include alkyl halides (e.g., methyl iodide), methyl p-toluenesulfonate, and trimethyloxonium tetrafluoroborate.

The amount of the alkylating agent to be used is usually 0.8 to 1.5 mol, and preferably 0.9 to 1.2 mol per mol of the compound (B-2).

When an alkyl halide or methyl p-toluenesulfonate is used, the reaction is preferably performed in the presence of a base. Examples of the base may include sodium hydride, sodium tert-butoxide, potassium tert-butoxide, silver (I) carbonate, potassium carbonate, sodium carbonate, triethylamine, isopropylethylamine, and the like.

The amount of the base to be used is usually 0.9 to 4 mol, and preferably 1.0 to 3.5 mol per mol of the compound (B-2).

Examples of the solvent may include ethers, alcohols, aromatic hydrocarbons, saturated hydrocarbons, amides, halogenated hydrocarbons, esters, ketones, nitriles, and the like.

The reaction is generally performed at −30 to 50° C., preferably −10 to 25° C.

The reaction time is generally from about 10 minutes to about 24 hours, and preferably from about 1 hour to about 8 hours.

An Embodiment [3]

An embodiment [3] of the present invention is a method for continuously performing Step (1), Step (2) and Step (3), which is a producing method characterized by obtaining the compound (B-2) or a salt thereof with high optical purity by optical resolution characterized by crystallizing a salt of the compound (B-1) and an optically active organic acid (Step (1)), obtaining the compound (C) or a salt thereof by subjecting the obtained compound (B-2) or a salt thereof to an alkylation reaction (Step (2)), and further obtaining the compound (X) or a salt thereof by subjecting the obtained compound (C) or a salt thereof to a reaction with the compound (D) or a salt thereof (Step (3)).

(1) Step (1) and Step (2)

In this embodiment, Step (1) can also be performed according to the method described in the above described embodiment [1], and Step (2) can be performed according to the method described in the above described embodiment [2].

(2) Step (3)

In Step (3), the reaction is performed by ureatizing the compound (C) or a salt thereof in the presence of the compound (D) or a salt thereof and, if desired, an activating agent and a base.

The amount of the compound (D) to be used is usually 0.7 to 2.0 mol, and preferably 0.9 to 1.5 mol per mol of the compound (C).

Examples of the activating agent may include chloroformate ester derivatives such as 2,2,2-trichloroethyl chloroformate, phenyl chloroformate or p-nitrophenyl chloroformate, triphosgene, phosgene, N, N'-carbonyldiimidazole or N, N'-disuccinimidyl carbonate, triphosgene and 2,2,2-trichloroethyl chloroformate are preferred.

The amount of the activating agent to be used is usually 0.3 to 1.5 mol, and preferably 0.4 to 1.0 mol per mol of the compound (C).

The base is preferably an organic base such as triethylamine or diisopropylethylamine. The amount of the base to be used is usually 0.8 to 5.0 mol, and preferably 1.0 to 3.5 mol per mol of the compound (C).

Examples of the solvent may include ethers, nitriles, amides, sulfoxides, and the like.

The reaction is generally performed at 0 to 150° C., preferably 10 to 120° C. The reaction time is generally from about 1 hour to about 48 hours, and preferably from about 2 hours to about 24 hours.

An Embodiment [4]

An embodiment [4] of the present invention is a method for continuously performing Step (A) and Step (1) which is a producing method characterized by obtaining the compound (B-1) or a salt thereof by subjecting the compound (A) or a salt thereof to 1) an asymmetric reduction of a carbonyl group or 2) an asymmetric reduction of a carbonyl group and a deprotection reaction of an amino protecting group (Step (A)), and obtaining the compound (B-2) or a salt thereof by optical resolution including crystallization of a salt of the compound (B-1) and an optically active organic acid (step (1)).

(1) Step (A)

Step (A) includes an asymmetric reduction step and, if desired, a deprotection step for an amino protecting group.

(Asymmetric Reduction Step)

The step includes subjecting the compound (A) or a salt thereof to an asymmetric reduction reaction to obtain the compound (B-1) or a salt thereof. The reaction is performed by allowing compound (A) or a salt thereof to react with a hydrogen source in the presence of an asymmetric catalyst or a catalyst and an asymmetric ligand in the solvent.

Examples of the hydrogen source may include ammonium formate, isopropyl alcohol, formic acid and hydrogen. The amount of the hydrogen source to be used is usually 1 to 100 mol, and preferably 5 to 20 mol per mol of the compound (A). When hydrogen gas is used, it should be used in large excess under atmospheric pressure or pressure.

Examples of the asymmetric catalysts may include chloro ((1S,2S)—N-(benzylsulfonyl)-1,2-diphenylethanediamine) (mesitylene)ruthenium(II)(RuCl((S,S)-$BnSO_2$dpen) (mesitylene)), chloro((1S,2S)—N-(2',6'-dimethylbenzylsulfonyl)-1,2-diphenylethanediamine) (mesitylene)ruthenium(II) (RuCl((S,S)-2',6'-$(CH_3)_2BnSO_2$dpen)((mesitylene)), chloro ((1S,2S)—N-(p-toluenesulfonyl)-1,2-diphenylethanediamine)(mesitylene)ruthenium (II) (RuCl ((S,S)-TsDPEN)(mesitylene)), chloro((1S,2S)—N-(isobutanesulfonyl)-1,2-diphenylethanediamine)(mesitylene) ruthenium (II) (RuCl((S,S)-i-$BuSO_2$DPEN) (mesitylene)), etc. The amount of the asymmetric catalysts to be used is usually 0.001 to 0.2 mol, and preferably 0.005 to 0.1 mol per mol of the compound (A).

Examples of the catalysts may include dichloro(benzene) ruthenium(II) dimer ($[RuCl_2(benzene)]_2$), bis(norbornadiene)rhodium(I) tetrafluoroborate ($[Rh(NBD)_2BF_4]$), chloronorbornadienrhodium(I) dimer ($[RhCl(NBD)]_2$), and the like. The amount of the catalysts to be used is usually 0.001 to 0.2 mol, and preferably 0.005 to 0.1 mol per mol of the compound (A).

Examples of the asymmetric ligands may include phosphine-based ligands such as (R)-(−)-4,12-bis(diphenylphosphino)-[2.2]-paracyclophane ((R)-PHANEPHOS) and (R)-1-[(S)-2-diphenylphosphinoferrocenyl]ethyl-di-tert.-butylphosphine ((R,S)-PPF-$PtBu_2$). The amount of the asymmetric ligands to be used is usually 0.001 to 0.2 mol, and preferably 0.005 to 0.1 mol per mol of the compound (A).

This reaction may be performed in the presence of the base, if desired. The amount of the base to be used is usually 0.1 to 5 mol, and preferably 0.2 to 1.0 mol per mol of the compound (A).

Examples of the solvent may include nitriles, alcohols, amides, aromatic hydrocarbons, organic bases, water and the like.

The reaction is generally performed at −10 to 100° C., preferably 50 to 80° C. The reaction time is generally from about 1 hour to about 72 hours, and preferably from about 2 hours to about 48 hours.

After the completion of the reaction, the compound (A) or a salt thereof may not be isolated or purified, and may be subjected to the next Step (1) as a reaction mixture or after usual post-treatment.

(Deprotection Step)

This step can be performed as necessary. A person skilled in the art can appropriately perform the step using an amino protecting group deprotection reaction (removal reaction) known in the art.

(2) Step (1)

In this embodiment, the Step (1) can be performed according to the method described in the above-mentioned embodiment [1].

An Embodiment [5]

An embodiment [5] of the present invention is a method for continuously performing Step (A), Step (1), Step (2) and Step (3), which is a producing method characterized by obtaining the compound (B-1) or a salt thereof by subjecting the compound (A) or a salt thereof to 1) an asymmetric reduction of a carbonyl group or 2) an asymmetric reduction of a carbonyl group and a deprotection reaction of an amino protecting group (Step (A)), obtaining the compound (B-2) having high optical purity or a salt thereof by optical resolution including crystallization of a salt of the compound (B-1) and an optically active organic acid (Step (1)), obtaining the compound (C) or a salt thereof by subjecting the obtained compound (B-2) or a salt thereof to an alkylation reaction (Step (2)), and obtaining the compound (X) or a salt thereof by subjecting the obtained compound (C) or a salt thereof to a reaction with the compound (D) or a salt thereof (Step (3)).

In this embodiment, the Step (1) to (3) can be performed according to the method described in the above-mentioned embodiment [1] to [4].

An Embodiment [8]

An embodiment [8] of the present invention is a producing method characterized by obtaining the compound (X) or a salt thereof by subjecting the compound (C) or a salt thereof which is obtained for example by appropriately combining Step (A), Step (1) and Step (2) of the present invention to a reaction with the compound (D) or a salt thereof (Step (3)).

In this embodiment, the Step (3) can be performed according to the method described in the above-mentioned embodiment [3].

An Embodiment [9]

An embodiment [9] of the present invention is a producing method characterized by obtaining the compound (C) or a salt thereof by subjecting the obtained compound (B-2) or a salt thereof which is obtained for example by appropriately combining the Step (A) and Step (1) of the present invention to an alkylation reaction (Step (2)), and obtaining a compound (X) or a salt thereof by subjecting the obtained compound (C) or a salt thereof to a reaction with compound (D) or a salt thereof (Step (3))

In this embodiment, the steps (2) and (3) can be performed according to the method described in the above-mentioned embodiments [2] and [3].

EXAMPLES

The present invention is further explained in detail by the following examples, examples of formulations, and test examples, which are not limited to the present invention, and may be changed within the scope not deviating from the scope of the present invention.

In the following examples, “room temperature” generally represents about 10° C. to about 35° C. The ratios shown for mixed solvents are volume ratios unless otherwise specified. % indicates weight % unless otherwise specified.

In silica gel column chromatography, aminopropylsilane bonded silica gel was used when NH was described, 3-(2, 3-dihydroxypropoxy)propylsilane bonded silica gel was used when Diol was described, N-(2-aminoethyl)-3-aminopropylsilane bonded silica gel was used when DiNH was described. In HPLC (high performance liquid chromatography), octadecyl bonded silica gel was used when C18 was described. Unless otherwise specified, the ratio of elution solvent is expressed as a volume ratio.

The following abbreviations are used in the following examples.

$Boc_2O$: di-tert-butyl bicarbonate
$CDCl_3$: deuterated chloroform
$^{13}C$ NMR: carbon nuclear magnetic resonance
DMSO-$d_6$: deuterated dimethyl sulfoxide
$^{1}H$ NMR: proton nuclear magnetic resonance
LC/MS: liquid chromatograph mass spectrometer
ESI: electrospray ionization
APCI: atmospheric chemical ionization
DBU: 1,8-diazabicyclo [5.4.0] undeca-7-ene
DIEA: diisopropylethylamine
DMAP: 4-dimethylaminopyridine
DMF: N,N-dimethylformamide
mp: melting point
DPPA: diphenylphosphoryl azide
MS: mass spectrum
$[M+H]^+$, $[M-H]^-$: molecular ion peak
M: molar concentration
N: normality
$Pd(OAc)_2$: palladium(II) acetate
SPhos: 2-dicyclohexylphosphino-2',6'-dimethoxybiphenyl
TEA: triethylamine
TFA: trifluoroacetic acid
THF: tetrahydrofuran $^{1}H$ and $^{13}C$ NMR were measured by Fourier transform NMR. ACD/SpecManager (product name), etc. were used for analysis. Peaks with very loose protons such as hydroxyl groups and amino groups are not described.

MS was determined by LC/MS. ESI or APCI methods were used for ionization. Data are expressed as the actual value (found). Usually, a molecular ion peak ($[M+H]^+$, $[M-H]^-$, etc.) is observed, but in the case of a compound having a tert-butoxycarbonyl group, a peak in which the tert-butoxycarbonyl group or tert-butyl group has been removed may be observed as a fragment ion. In the case of a compound having a hydroxyl group, a peak from which $H_2O$ is removed may be observed as a fragment ion. In the case of salts, free molecular ion peaks or fragment ion peaks are usually observed.

[A Method for Producing the Compound (X) Described in International Application Number: PCT/JP2019/046261]

Reference Example 1

6-(2H-1,2,3-triazole-2-yl)-5-(trifluoromethyl)pyridine-3-amine

A) 5-nitro-2-(2H-1,2,3-triazole-2-yl)-3-(trifluoromethyl) pyridine

To a mixture of 2-chloro-5-nitro-3-(trifluoromethyl) pyridine (3.0 g) and THF (15 mL) was added 2H-1,2,3-triazole (0.921 mL) at room temperature, and the reaction mixture was stirred at the same temperature for 2 hours. The reaction mixture was diluted with water and the aqueous layer was extracted with ethyl acetate. The organic layer was washed with water and saturated brine, dried over anhydrous sodium sulfate, and the solvent was evaporated under reduced pressure. The residue was purified by silica gel column chromatography (ethyl acetate/hexane) to give the title compound (2.75 g).

MS: $[M+H]^+$ 259.9.

B) 6-(2H-1,2,3-triazole-2-yl)-5-(trifluoromethyl) pyridine-3-amine

To a mixture of 5-nitro-2-(2H-1,2,3-triazole-2-yl)-3-(trifluoromethyl)pyridine (3.54 g), 10% hydrochloric acid/methanol solution (101 mL) and methanol (100 mL) was added tin (II) chloride (12.95 g) at room temperature, and the reaction mixture was stirred at the same temperature for 2 hours. The solvent was evaporated under reduced pressure, and ethyl acetate was added to the residue. The mixture was neutralized with 2N aqueous sodium hydroxide solution. The precipitate was filtered, and the aqueous layer of the filtrate was extracted with ethyl acetate. The organic layer was washed with water and saturated brine, dried over anhydrous sodium sulfate, and the solvent was evaporated under reduced pressure. The residue was purified by silica gel column chromatography (ethyl acetate/hexane) to give the title compound (2.95 g).

MS: $[M+H]^+$ 229.9.

Reference Example 2

(S)—N-(6-chloro-4-(1-methoxyethyl)-1,5-naphthyridine-3-yl)-N'-(6-(2H-1,2,3-triazole-2-yl)-5-(trifluoromethyl)pyridine-3-yl)urea

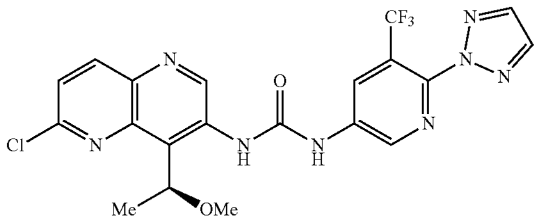 [SMILES: CO[C@@H](C)c1c(NC(=O)Nc2cnc(-n3nccn3)c(C(F)(F)F)c2)cnc2ccc(Cl)nc12]

A) tert-butyl(6-chloro-2-(2-methoxypropanoyl)pyridine-3-yl) carbamate

To a mixture of tert-butyl(2-bromo-6-chloropyridine-3-yl) carbamate (20.0 g) and THF (160 mL) was added 1.08 M methyllithium/diethyl ether solution (72.3 mL) at −78° C., and the reaction mixture was stirred at the same temperature for 15 minutes. To the reaction mixture was added 1.6 M n-butyllithium/hexane solution (52.8 mL) at −78° C., and the reaction mixture was stirred at the same temperature for 15 minutes. To the reaction mixture was added a solution of 2-methoxy-1-morpholinopropane-1-on (16.9 g) in THF (60 mL) at −78° C., and the reaction mixture was warmed to room temperature under stirring for 2 hours. To the reaction mixture was added a solution of acetic acid (15 mL) in water (150 mL) at room temperature, and the aqueous layer was extracted with ethyl acetate. The organic layer was washed with saturated aqueous sodium bicarbonate solution and saturated brine, dried over anhydrous magnesium sulfate, and the solvent was evaporated under reduced pressure. The residue was purified by silica gel column chromatography (ethyl acetate/hexane) to give the title compound (15.81 g).

MS: $[M+H-tBu]^+$258.9.

B) 1-(6-chloro-3-((2-nitrovinyl)amino)pyridine-2-yl)-2-methoxypropane-1-one

To a mixture of tert-butyl(6-chloro-2-(2-methoxypropanoyl) pyridine-3-yl)carbamate (15.7 g) and ethyl acetate (100 mL) was added 4N hydrogen chloride/cyclopentyl methyl ether solution (200 mL) at room temperature, and the reaction mixture was stirred at the same temperature for 2 hours. To the reaction mixture was further added 4N hydrogen chloride/cyclopentyl methyl ether solution (100 mL) at room temperature, the mixture was stirred at the same temperature overnight, and the solvent was evaporated under reduced pressure. A mixture of the obtained residue, (E)-4-(2-nitrovinyl)morpholine (9.47 g), 6N hydrochloric acid (36 mL) and acetone (120 mL) was stirred at room temperature for 3 hours. The reaction mixture was diluted with water (240 mL) and stirred at 0° C. for 1 hour. The precipitate was collected by filtration, washed with water, and the obtained solid was dried under reduced pressure to give the title compound (12.55 g).

MS: $[M+H]^+$ 286.0.

C) 2-chloro-8-(1-methoxyethyl)-7-nitro-1,5-naphthyridine

To a mixture of DBU (6.62 mL) and THF (120 mL) was added a solution of 1-(6-chloro-3-((2-nitrovinyl)amino)pyridine-2-yl)-2-methoxypropane-1-one (12.55 g) in THF (280 mL) at room temperature, and the reaction mixture was stirred at the same temperature for 1 hour. The reaction mixture was adjusted to a slightly acidic pH with 2N hydrochloric acid, diluted with water, and the aqueous layer was extracted with ethyl acetate. The organic layer was washed with saturated brine, dried over anhydrous magnesium sulfate, and the solvent was evaporated under reduced pressure. The residue was purified by silica gel column chromatography (ethyl acetate/hexane) to give the title compound (9.82 g).

MS: $[M+H]^+$ 267.9.

D) 6-chloro-4-(1-methoxyethyl)-1,5-naphthyridine-3-amine

A mixture of 2-chloro-8-(1-methoxyethyl)-7-nitro-1,5-naphthyridine (5.00 g), tin (II) chloride dihydrate (21.1 g) and ethyl acetate (150 mL) was stirred at 60° C. for 2 hours, and then stirred at room temperature overnight. The reaction mixture was diluted with ethyl acetate, and the mixture was neutralized with 2 M aqueous potassium carbonate solution. The precipitate was filtered, and the aqueous layer of the filtrate was extracted with ethyl acetate. The organic layer was washed with saturated brine, dried over anhydrous magnesium sulfate, and the solvent was evaporated under reduced pressure. The residue was purified by silica gel column chromatography (NH, ethyl acetate/hexane) to give the title compound (3.91 g).

MS: $[M+H]^+$ 238.0.

E) (S)-6-chloro-4-(1-methoxyethyl)-1,5-naphthyridine-3-amine

6-Chloro-4-(1-methoxyethyl)-1,5-naphthyridine-3-amine (3.84 g) was fractionated by HPLC (CHIRALPAK IG(VJ003), 20 mmID×250 mmL, mobile phase: hexane/ethanol=900/100), and the larger retention fraction containing the desired product was concentrated under reduced pressure to give the title compound (1865 mg).

Optical purity: 99.9% ee, retention time: 7.359 minutes (CHIRALPAK AD-H (VJ019), 4.6 mmID×250 mmL, mobile phase: hexane/2-propanol=850/150) MS: $[M+H]^+$ 238.0.

The absolute configuration was determined using a single-crystal X-ray diffractometer.

F) (S)—N-(6-chloro-4-(1-methoxyethyl)-1,5-naphthyridine-3-yl)-N'-(6-(2H-1, 2, 3-triazole-2-yl)-5-(trifluoromethyl) pyridine-3-yl)urea The reaction was performed in 4 steps as follows.

Reaction mixture 1: To a mixture of triphosgene (62 mg) and THF (5 mL) was added a solution of (S)-6-chloro-4-(1-methoxyethyl)-1,5-naphthyridine-3-amine (100 mg) and DIEA (0.220 mL) in THF (2 mL) at 0° C., and the reaction mixture was stirred at the same temperature for 1 hour. To the reaction mixture was added 6-(2H-1,2,3-triazole-2-yl)-5-(trifluoromethyl)pyridine-3-amine (106 mg) obtained in Reference Example 1 at 0° C., and the reaction mixture was stirred at 60° C. overnight.

Reaction mixture 2: To a mixture of triphosgene (187 mg) and THF (12 mL) was added a solution of (S)-6-chloro-4-(1-methoxyethyl)-1,5-naphthyridine-3-amine (300 mg) and DIEA (0.660 mL) in THF (6 mL) at 0° C., and the reaction mixture was stirred at the same temperature for 1 hour. To the reaction mixture was added 6-(2H-1,2,3-triazole-2-yl)-5-(trifluoromethyl)pyridine-3-amine (318 mg) obtained in Reference Example 1 at 0° C., and the reaction mixture was stirred at 60° C. for 2 hours. To the reaction mixture was added 6-(2H-1,2,3-triazole-2-yl)-5-(trifluoromethyl) pyridine-3-amine (29 mg) at the same temperature, and the reaction mixture was stirred overnight.

Reaction mixture 3: To a mixture of triphosgene (375 mg) and THF (24 mL) was added a solution of (S)-6-chloro-4-(1-methoxyethyl)-1,5-naphthyridine-3-amine (600 mg) and DIEA (1.32 mL) in THF (12 mL) at 0° C., and the reaction mixture was stirred at the same temperature for 1 hour. To the reaction mixture was added 6-(2H-1,2,3-triazole-2-yl)-5-(trifluoromethyl)pyridine-3-amine (636 mg) obtained in Reference Example 1 at 0° C., and the reaction mixture was stirred at 60° C. for 2 hours. To the reaction mixture was added 6-(2H-1,2,3-triazole-2-yl)-5-(trifluoromethyl) pyridine-3-amine (116 mg) at the same temperature, and the reaction mixture was stirred overnight.

Reaction mixture 4: To a mixture of triphosgene (531 mg) and THF (34 mL) was added a solution of (S)-6-chloro-4-(1-methoxyethyl)-1,5-naphthyridine-3-amine (850 mg) and DIEA (1.87 mL) in THF (17 mL) at 0° C., and the reaction mixture was stirred at the same temperature for 1 hour. To the reaction mixture was added 6-(2H-1,2,3-triazole-2-yl)-5-(trifluoromethyl)pyridine-3-amine (901 mg) obtained in Reference Example 1 at 0° C., and the reaction mixture was stirred at 60° C. for 2 hours. To the reaction mixture was added 6-(2H-1,2,3-triazole-2-yl)-5-(trifluoromethyl) pyridine-3-amine (164 mg) at the same temperature, and the reaction mixture was stirred overnight.

The reaction mixture 1-4 was combined into one, the mixture was diluted with saturated aqueous sodium hydrogen carbonate solution, and the aqueous layer was extracted with ethyl acetate. The organic layer was washed with saturated brine, dried over anhydrous magnesium sulfate, and the solvent was evaporated under reduced pressure. To the obtained residue were added THF and ethyl acetate, and the insoluble residue was filtered off and the filtrate was concentrated under reduced pressure. The residue was purified by silica gel column chromatography (NH, ethyl acetate/hexane), whereby a crude crystal (3.46 g) was obtained. The obtained crude crystal was dissolved in ethyl acetate (20 mL) at 80° C., and n-heptane (180 mL) was added dropwise to the mixed solution at the same temperature. The mixed solution was stirred at the same temperature for 1 hour, cooled to room temperature, and stirred at the same temperature overnight. The precipitate was collected by filtration, washed with a mixed solution of ethyl acetate and n-heptane, and dried under reduced pressure to give the title compound (3.35 g).

$^1$H NMR (300 MHz, DMSO-$d_6$) δ 1.56 (3H, d, J=6.4 Hz), 3.36 (3H, s), 5.85 (1H, q, J=6.7 Hz), 7.77 (1H, d, J=8.7 Hz), 8.18 (2H, s), 8.46 (1H, d, J=9.1 Hz), 8.74 (1H, d, J=2.6 Hz), 8.89 (1H, d, J=2.3 Hz), 9.24 (1H, s), 9.68 (1H, s), 10.89 (1H, s).

MS: $[M+H]^+$ 491.1

The absolute configuration was determined using a single-crystal X-ray diffractometer.

Reference Example 3

(S)—N-(4-(1-methoxyethyl)-6-methyl-1,5-naphthyridine-3-yl)-N'-(6-(2H-1,2,3-triazole-2-yl)-5-(trifluoromethyl) pyridine-3-yl)urea

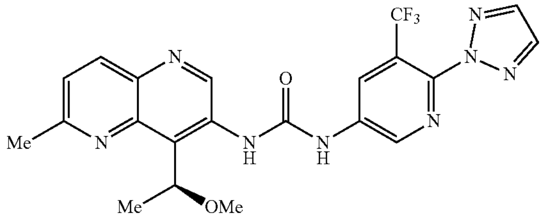 [SMILES: CO[C@@H](C)c1c(NC(=O)Nc2cnc(-n3nccn3)c(C(F)(F)F)c2)cnc2ccc(C)nc12]

A) 8-(1-methoxyethyl)-2-methyl-7-nitro-1,5-naphthyridine

A mixture of 2-chloro-8-(1-methoxyethyl)-7-nitro-1,5-naphthyridine (500 mg), 2,4,6-trimethylboroxine (0.39 mL), $Pd(dppf)Cl_2 \cdot CH_2Cl_2$ (153 mg), tripotassium phosphate (793 mg) and 1,2-dimethoxyethane (20 mL) was heated at 100° C. for 1.5 hours under microwave irradiation. The reaction mixture was diluted with ethyl acetate. The insoluble substance was filtered through Celite, and washed with ethyl acetate. The filtrate was concentrated under reduced pressure. The residue was purified by silica gel column chromatography (ethyl acetate/hexane) to give the title compound (439 mg).

MS: $[M+H]^+$ 247.9

B) 4-(1-methoxyethyl)-6-methyl-1,5-naphthyridine-3-amine

A mixture of 8-(1-methoxyethyl)-2-methyl-7-nitro-1,5-naphthyridine (470 mg), tin(II) chloride dihydrate (2.57 g), THF (3 mL) and ethanol (12 mL) was stirred at room temperature overnight at 60° C. for 7 hours. The reaction mixture was diluted with ethyl acetate and neutralized with saturated aqueous sodium bicarbonate solution. The insoluble substance was filtered and washed with ethyl acetate. The filtrate was extracted twice with ethyl acetate. The organic layer was washed with saturated brine, dried over anhydrous magnesium sulfate, and the solvent was evaporated under reduced pressure. The residue was purified by silica gel column chromatography (ethyl acetate/hexane) followed by silica gel column chromatography (NH, ethyl acetate/hexane), whereby the title compound (306 mg) was obtained.

MS: $[M+H]^+$ 217.9

C) N-(4-(1-methoxyethyl)-6-methyl-1,5-naphthyridine-3-yl)-N'-(6-(2H-1,2,3-triazole-2-yl)-5-(trifluoromethyl)pyridine-3-yl)urea To a solution of 4-(1-methoxyethyl)-6-methyl-1,5-naphthyridine-3-amine (80 mg), 6-(2H-1,2,3-triazole-2-yl)-5-(trifluoromethyl)pyridine-3-amine (101 mg) obtained in Reference Example 1 and pyridine (0.089 mL) in THF (5 mL) was added a solution of triphosgene (54.6 mg) in THF (1 mL) at 0° C. The reaction mixture was stirred at 0° C. for 30 minutes. The reaction mixture was added pyridine at 0° C. for 30 minutes followed by triphosgene (54.6 mg) in THF (1 mL). The reaction mixture was stirred at 0° C. for 30 minutes and at room temperature for 4 hours. The mixture was added to a saturated aqueous sodium bicarbonate solution, and extracted twice with ethyl acetate. The organic layer was washed with saturated brine, dried over anhydrous magnesium sulfate, and the solvent was evaporated under reduced pressure. The residue was purified by silica gel column chromatography (NH, ethyl acetate/hexane) to give the title compound (127 mg).

MS: $[M+H]^+$ 473.1

D) (S)—N-(4-(1-methoxyethyl)-6-methyl-1,5-naphthyridine-3-yl)-N'-(6-(2H-1, 2, 3-triazole-2-yl)-5-(trifluoromethyl) pyridine-3-yl)urea N-(4-(1-Methoxyethyl)-6-methyl-1,5-naphthyridine-3-yl)-N'-(6-(2H-1,2,3-triazole-2-yl)-5-(trifluoromethyl)pyridine-3-yl)urea (119.8 mg) was fractionated by HPLC (CHIRALPAK AD-H (VA001), 20 mmID×250 mmL, mobile phase: hexane/ethanol=700/300), and the smaller retention time fraction containing the objective compound was concentrated under reduced pressure to give the title compound (55.6 mg).

MS: $[M+H]^+$ 473.1

[A Method for Producing Compound (X) According to the Present Invention]

Producing Example 1

Phenyl 6-(2H-1,2,3-triazole-2-yl)-5-(trifluoromethyl) pyridine-3-aminocarbamate

A) 5-nitro-2-(2H-1,2,3-triazole-2-yl)-3-(trifluoromethyl) pyridine

To a solution of 2-chloro-5-nitro-3-(trifluoromethyl) pyridine (30 g) in 2-propanol (150 mL) was added 1H-1,2,3-triazole (8.44 mL), potassium carbonate (27.45 g) and 2-propanol (210 mL) at room temperature, and the reaction mixture was stirred at the same temperature for 7 hours.

Water (270 mL) was added to the reaction mixture, and the mixture was stirred at the same temperature for 16 hours. The obtained solid was collected by filtration, washed with water (150 mL), and dried at 55° C. overnight to give the title compound (26.43 g).

$^1$H NMR (500 MHz, $CDCl_3$) δ 8.06 (2H, s), 9.06 (1H, s), 9.59 (1H, s).

A-1) To a mixed solution of 2-chloro-5-nitro-3-(trifluoromethyl)pyridine (7.98 kg) and 2-propanol (75.0 kg) was added 1H-1,2,3-triazole (2.90 kg) and potassium carbonate (7.30 kg) at room temperature, and the reaction mixture was stirred at the same temperature for 12 hours. Water (72.0 kg) was added to the reaction mixture, and the mixture was stirred at the same temperature for 3 hours. The obtained solid was collected by filtration, washed with water (39.9 kg), and dried at 55° C. overnight to give the title compound (7.23 kg).

B) 6-(2H-1,2,3-Triazole-2-yl)-5-(trifluoromethyl) pyridine-3-amine

A mixture of 5-nitro-2-(2H-1,2,3-triazole-2-yl)-3-(trifluoromethyl)pyridine (25 g), 10% palladium-carbon (K type) (2.5 g) and methanol (625 mL) was added to an autoclave, and the mixture was stirred at 0.5 MPa of hydrogen pressure and 55° C. for 8 hours. The mixture was filtered and washed with methanol (50 mL). The filtrate was concentrated to 50 mL, and then, water (110 mL), seed crystals and water (115 mL) were added thereto in this order at 5° C., and the mixture was stirred at the same temperature for 3 hours. The obtained solid was filtered, washed with water (100 mL) and dried overnight at 55° C. to give the title compound (20.16 g).

$^1$H NMR (500 MHz, $CDCl_3$) δ 4.56 (2H, br s), 7.30 (1H, s), 7.87 (2H, s), 8.03 (1H, br s).

B-1) A mixture of 5-nitro-2-(2H-1,2,3-triazole-2-yl)-3-(trifluoromethyl)pyridine (7.14 kg), 10% palladium-carbon (K-type) (0.72 kg) and methanol (142.6 kg) was added to an autoclave, and the mixture was stirred at 0.5 MPa of hydrogen pressure and 55° C. for 8 hours after nitrogen substitution. The mixture was filtered and washed with methanol (11.4 kg). The filtrate was concentrated under reduced pressure to about 14 L, and then, water (32.0 kg), seed crystals and water (32.8 kg) were added thereto in this order at 5° C., and the mixture was stirred at the same temperature for 3 hours. The obtained solid was filtered, washed with water (28.8 kg) and dried overnight at 55° C. to give the title compound (5.55 kg).

C) Phenyl 6-(2H-1,2,3-triazole-2-yl)-5-(trifluoromethyl) pyridine-3-aminocarbamate To a mixture of 6-(2H-1,2,3-triazole-2-yl)-5-(trifluoromethyl)pyridine-3-amine (15 g), acetonitrile (45 mL) and pyridine (10.35 g) under nitrogen atmosphere was added phenyl chlorocarbonate (11.27 g) at 5° C., and the mixture was stirred at the same temperature for 1 hour. Ethanol (15 mL), water (105 mL) and seed crystals were added, and the mixture was further stirred at the same temperature for 3 hours. The obtained solid was collected by filtration, washed with ethanol/water (1/1, 45 mL), and dried at 55° C. overnight to give the title compound (21.47 g).

$^1$H NMR (500 MHz, $CDCl_3$) δ 7.14-7.19 (2H, m), 7.25-7.30 (1H, m), 7.37-7.45 (2H, m), 7.94 (2H, s), 8.61 (1H, br s), 8.69 (1H, d, J=2.52 Hz).

C-1) To a mixture of 6-(2H-1,2,3-triazole-2-yl)-5-(trifluoromethyl)pyridine-3-amine (5.01 kg), acetonitrile (11.8 kg) and pyridine (3.49 kg) under nitrogen atmosphere was added phenyl chlorocarbonate (3.80 kg) at 5° C., and the mixture was stirred at the same temperature for 1 hour. Phenyl chlorocarbonate (0.30 kg) was added at the same temperature, and the mixture was stirred at the same temperature for 1 hour. Phenyl chlorocarbonate (0.29 kg) was added at the same temperature, and the mixture was stirred at the same temperature for 1 hour. Ethanol (3.90 kg), water (35.00 kg) and seed crystals (5 g) were added to the mixture at the same temperature, and the mixture was stirred at the same temperature for 3 hours. The obtained solid was collected by filtration, washed with a mixed solution of ethanol (5.90 kg) and water (7.55 kg), and then dried at 55° C. overnight to give the title compound (7.22 kg).

Producing Example 2

4-acetyl-6-chloro-1,5-naphthyridine-3-amine

A) (E)-4-(2-nitrovinyl)morpholine

A mixture of nitromethane (461 mL), triethyl orthoformate (510 mL), p-toluenesulfonic acid monohydrate (9.83 g) and morpholine (150 g) was stirred under nitrogen atmosphere at 80° C. for 4 hours. After cooling to 50° C., the mixture was added ethanol (150 mL) and concentrated under reduced pressure to about 300 mL again. To the obtained mixture was added a mixture of methyl tert-butyl ether (600 mL) and ethanol (60 mL), and the mixture was stirred at room temperature for a suspension for 2 hours. The obtained solid was collected by filtration, washed with a mixed solvent of methyl tert-butyl ether and ethanol (10/1, 300 mL), and dried under reduced pressure at 35° C. to give the title compound (242 g).

$^1$H NMR (500 MHz, $CDCl_3$) δ 3.20-3.50 (4H, br s), 3.73-3.84 (4H, m), 6.74 (1H, d, J=10.72 Hz), 8.10 (1H, d, J=11.03 Hz).

B) 3-(2-(E)-nitrovinylamino)-6-chloropyridine-2-carboxylic acid

To a mixture of 3-amino-6-chloropyridine-2-carboxylic acid (100 g), (E)-4-(2-nitrovinyl)morpholine (110 g) and acetone (900 mL) was added 6 M hydrochloric acid (483 mL) at 20-28° C., and the mixture was stirred at room temperature for 3.5 hours. To the reaction mixture was added 4 M aqueous sodium hydroxide solution (670 mL), and the mixture was stirred for 2 hours. The obtained solid was collected by filtration, washed with acetone/water (1/4, 500 mL) and then dried under reduced pressure at 60° C. to give the title compound (162.3 g).

$^1$H NMR (500 MHz, DMSO-$d_6$) δ(E/Z mixture) (main product) 6.69 (1H, d, J=6.31 Hz), 7.54 (1H, d, J=8.51 Hz), 8.01-8.10 (1H, m), 8.15 (1H, d, J=8.51 Hz), 14.61 (1H, d, J=15.00 Hz).

(by-product) 7.37 (1H, d, J=10.72 Hz) 7.47 (1H, d, J=8.83 Hz), 8.72 (1H, d, J=10.72 Hz).

C) 6-chloro-3-nitro-1,5-naphthyridine-4-ol

A mixture of 3-(2-(E)-nitrovinylamino)-6-chloropyridine-2-carboxylic acid (160 g), potassium acetate (79.93 g) and acetic anhydride (800 mL) was stirred under nitrogen atmosphere at 80° C. for 4 hours. The reaction mixture was cooled to 50° C. and water (800 mL) was added between 45° C. and 62° C. The mixture was stirred at 50° C. for 1 hour and at room temperature for 1.5 hours, and then the obtained solid was collected by filtration, washed with acetone/water (1/4, 800 mL), and dried at 60° C. to give the title compound (105.2 g).

$^1$H NMR (500 MHz, DMSO-$d_6$) δ 7.88 (1H, d, J=8.51 Hz), 8.20 (1H, d, J=8.83 Hz), 9.28 (1H, s), 12.17-13.95 (1H, m).

D) 8-bromo-2-chloro-7-nitro-1,5-naphthyridine

To a suspension of 6-chloro-3-nitro-1,5-naphthyridine-4-ol (35.0 g) in DMF (345 mL) was added phosphorus tribromide (63.1 g) at 5±5° C. under a nitrogen atmosphere. The reaction mixture was stirred at the same temperature for 4 hours. The reaction mixture was added to water (630 mL) cooled to 5±5° C., and further 8 M aqueous sodium hydroxide solution (69.8 mL) was added. The obtained suspension was stirred at 25±5° C. for 15 hours. The obtained solid was collected by filtration, washed with water (175 mL), dried under nitrogen. To a suspension of the obtained solid in ethanol (175 mL) was added water (350 mL), and the mixture was stirred at 25±5° C. for 1 hour. The obtained solid was collected by filtration, washed with ethanol (175 mL), dried under nitrogen for 1 hour to give the title compound (42.52 g).

$^1$H NMR (500 MHz, DMSO-$d_6$) δ 8.11 (1H, d, J=8.51 Hz), 8.66 (1H, d, J=8.83 Hz), 9.41 (1H, s).

E) 2-chloro-8-(1-ethoxyvinyl)-7-nitro-1,5-naphthyridine

A solution of 8-bromo-2-chloro-7-nitro-1,5-naphthyridine (24.5 g) and tributyl(1-ethoxyvinyl)tin (33.7 g) in DME (245 mL) was degassed, purged with nitrogen, and $PdCl_2(Amphos)_2$ (1.2 g) was added thereto, and the mixture was stirred at 80° C. for 2 hours. To the reaction mixture was added a solution of potassium fluoride (49.3 g) in water (245 mL) at room temperature, and the mixture was stirred at room temperature for an hour. After the reaction mixture was filtered, the obtained insoluble substance was washed with toluene (108 mL), and the filtrate was concentrated under reduced pressure to about 370 mL. Toluene (245 mL) was added to separate the organic layer, and the obtained organic layer was washed with 10% brine twice. The organic layer was passed through silica gel (Wakogel (Registered Trademark) FC-40, 25 g) and eluted with toluene (50 mL). The eluate was concentrated under reduced pressure and diluted with acetone (135 mL). Activated charcoal Shirasagi A (4.9 g) was added, and the mixture was stirred at room temperature for 20 minutes. Activated carbon was filtered and concentrated under reduced pressure. The obtained residue was suspended in 2-propanol (49 mL), and the mixture was stirred for 1 hour. The obtained solid was collected by filtration, washed with 2-propanol (24.5 mL), and dried under reduced pressure at 60° C. to give the title compound (17.14 g).

$^1$H NMR (500 MHz, DMSO-$d_6$) δ 1.27 (1H, t, J=6.94 Hz), 3.98 (2H, q, J=6.94 Hz), 4.73 (1H, d, J=3.15 Hz), 4.98 (1H, d, J=3.15 Hz), 8.05 (1H, d, J=8.83 Hz), 8.61 (1H, d, J=8.83 Hz), 9.44 (1H, s).

F) 8-acetyl-2-chloro-7-nitro-1,5-naphthyridine

To a solution of 2-chloro-8-(1-ethoxyvinyl)-7-nitro-1,5-naphthyridine (15 g) in acetone (60 mL) was added 6 M hydrochloric acid (11 mL) at 22 to 26° C., and the mixture was stirred at room temperature for 4 hours. To the reaction mixture was added 1 M aqueous sodium hydroxide solution (70 mL) and water (99 mL), and the mixture was stirred at room temperature for 1 hour. The obtained solid was collected by filtration, washed with acetone/water (1/3, 75 mL), and dried under reduced pressure at 60° C. to 13.06 g. A mixture of the obtained solid and ethyl acetate (45 mL) was heated at 60° C. To the reaction mixture was added heptane (75 mL), and the mixture was stirred at 5° C. for 1.5 hours. The obtained solid was collected by filtration, washed with heptane (75 mL), and dried under reduced pressure at 60° C. to give the title compound (11.21 g).

$^1$H NMR (500 MHz, DMSO-$d_6$) δ 2.72 (3H, s), 8.14 (1H, d, J=8.83 Hz), 8.70 (1H, d, J=8.83 Hz), 9.70 (1H, s).

G) 4-acetyl-6-chloro-1,5-naphthyridine-3-amine

8-Acetyl-2-chloro-7-nitro-1,5-naphthyridine (13.0 g), 5% palladium-carbon (PE type 1.30 g) and methanol (221 mL) were added to an autoclave, cooled to 15° C., and stirred at 0.20 MPa of hydrogen pressure for 6 hours. After releasing hydrogen into the atmosphere, tetrahydrofuran (130 mL) was added and the mixture was warmed to 50° C. The obtained solution was stirred at 50° C. for 20 minutes, and then the catalyst was filtered and washed with tetrahydrofuran (52 mL). The filtrate was concentrated to about 52 mL under reduced pressure, and methanol (130 mL) was added. This operation was repeated. The filtrate was concentrated to about 65 mL under reduced pressure and warmed to 60° C. Water (130 mL) was added to the mixture at 60° C., then the mixture was stirred at the same temperature for 1 hour. After the mixture was stirred at room temperature for 12 hours, the obtained solid was filtered and washed with methanol/water (1/2, 39 mL). The solid was dried under reduced pressure at 60° C. to give the title compound (9.91 g).

$^1$H NMR (500 MHz, DMSO-$d_6$) δ 2.82 (3H, s), 7.44 (1H, d, J=8.51 Hz), 7.94 (2H, s), 8.21 (1H, d, J=8.51 Hz), 8.70 (1H, s).

H) di-tert-butyl 4-acetyl-6-chloro-1,5-naphthyridine-3-aminodicarbamate

To a solution of 4-acetyl-6-chloro-1,5-naphthyridine-3 amine (27 g) in THF (270 mL) was added $Boc_2O$ (57.96 g), triethylamine (50.48 mL) and DMAP (147.48 mg) at 0 to 5° C. The reaction mixture was stirred at 50° C. for 3 hours. The reaction mixture was diluted with water and extracted twice with ethyl acetate. The organic layer was washed with saturated brine, dried over sodium sulfate, and concentrated under reduced pressure. The residue was purified by silica gel column chromatography (ethyl acetate/hexane), and crystallized with ethyl acetate/hexane to give the title compound (35 g).

MS: $[M+H]^+$ 422.1

Example 1

(S)-6-chloro-4-(1-hydroxyethyl)-1,5-naphthyridine-3-amine

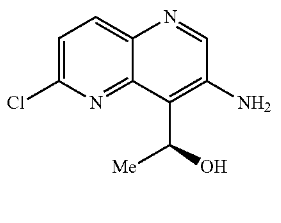 [SMILES: C[C@H](O)c1c(N)cnc2ccc(Cl)nc12]

A mixture of di-tert-butyl 4-acetyl-6-chloro-1,5-naphthyridine-3-aminodicarbamate (10 g), potassium formate (19.96 g), chloro((1S,2S)—N-(benzylsulfonyl)-1,2-diphenylethanediamine)(mesitylene)ruthenium(II) (294.96 mg), tert-amyl alcohol (50 mL) and water (25 mL) was degassed with argon, and stirred at 50° C. for 48 hours. The reaction mixture was added to water and extracted twice with ethyl acetate. The organic layer was washed with water and then saturated brine, dried over sodium sulfate, and concentrated under reduced pressure.

The residue was dissolved in toluene, filtered through silica gel, and concentrated under reduced pressure. The obtained residue was dissolved in cyclopentylmethyl ether (50 mL), and a solution of 4 M hydrogen chloride in cyclopentylmethyl ether (100 mL) was added at 0° C. The reaction mixture was stirred at room temperature overnight and the obtained solid was collected by filtration. The obtained solid was neutralized with a saturated aqueous sodium bicarbonate solution, and extracted with ethyl acetate/THF. The organic layer was washed with water and then saturated brine, dried over sodium sulfate, and concentrated under reduced pressure.

The residue was dissolved in isopropyl acetate (150 mL) at 50° C. To the obtained solution was added a solution of D-(−)-tartaric acid (1.6 g) in ethanol (20 mL) at 50° C., and the mixture was stirred at the same temperature for 1 hour. Isopropyl acetate was added and the mixture was stirred at room temperature overnight. The obtained solid was collected by filtration and washed with isopropyl acetate to give the title compound, hemi-D-(−)-tartrate (4.4 g, 97.2% ee). The obtained hemi-D-(−)-tartrate was neutralized with a saturated aqueous sodium bicarbonate solution and extracted with ethyl acetate/THF. The organic layer was washed with water and then saturated brine, dried over sodium sulfate, and then concentrated under reduced pressure to give the title compound (3.27 g).

MS: $[M+H]^+$ 224.1

Example 2

(S)-6-chloro-4-(1-hydroxyethyl)-1,5-naphthyridine-3-amine hemi-D-(−)-tartrate

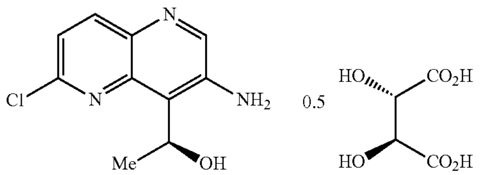 [SMILES: C[C@H](O)c1c(N)cnc2ccc(Cl)nc12 ; O=C(O)[C@@H](O)[C@H](O)C(=O)O]

(1) $[RuCl_2(benzene)]_2$ (214.4 mg), (R)-PHANEPHOS (593.2 mg), and 4-acetyl-6-chloro-1,5-naphthyridine-3-amine (9.50 g) were charged into an autoclave, and the mixture of cyclohexylamine (2.443 mL) and deoxygenated ethanol (380 mL) was added after nitrogen substitution. The mixture was heated to 60° C. under a hydrogen pressure of 0.5 MPa. The reaction mixture was stirred at 60° C. for 16 hours after changing the hydrogen pressure to 0.95 MPa. After cooling to 50° C., hydrogen was allowed to escape and the mixture was concentrated under reduced pressure to about 143 mL.

To the obtained residue was added 4 M hydrochloric acid (16.1 mL), and the mixture was stirred at room temperature for 3 hours. The obtained solid was collected by filtration and washed with a cold ethanol (66.5 mL). The solid was dried under reduced pressure at 60° C. to give 3.76 g of solid. A mixture of the obtained solid (3.50 g) and water (122.5 mL) was stirred for 20 minutes. The solid was filtered and washed with water (17.5 mL). To the filtrate was added isopropyl acetate (35 mL) and 8 M aqueous sodium hydroxide solution (1.682 mL) at room temperature, and the mixture was stirred. The organic layer was separated, warmed to 40° C., and then added a hot solution of D-(−)-tartaric acid (1.21 g) in hot ethanol (8.8 mL). Heptane (26.3 mL) was added and the mixture was stirred at 40° C. for 3.5 hours and at room temperature for 66 hours. The obtained solid was collected by filtration and washed with isopropyl acetate/heptane/ethanol (4/2/1, 24.5 mL). The drying under reduced pressure at 60° C. gave the title compound (2.80 g, >99.9% ee).

$^1H$ NMR (500 MHz, DMSO-$d_6$) δ 1.40 (3H, d, J=6.62 Hz), 4.33 (1H, s), 5.73 (1H, br s), 5.97 (1H, q, J=6.62 Hz), 6.29 (2H, br s), 7.37 (1H, d, J=8.51 Hz), 8.17 (1H, d, J=8.83 Hz), 8.54 (1H, s).

(2) $[RuCl_2(benzene)]_2$ (338.5 g), (R)-PHANEPHOS (936.6 g), and 4-acetyl-6-chloro-1,5-naphthyridine-3-amine (15.0 kg) were charged into a 500 L pressurization reactor, and after nitrogen substitution, a mixture of cyclohexylamine (3.36 kg) and deoxygenated ethanol (474 kg) was added. The mixture was heated to 60° C. under a hydrogen pressure of 0.5 MPa. The reaction mixture was stirred at 60° C. for 23 hours after changing the hydrogen pressure to 0.95 MPa. After cooling to 30° C., hydrogen was allowed to escape and the mixture was concentrated under reduced pressure to about 150 L.

To the obtained residue was added 4 M hydrochloric acid (23.7 kg), and the mixture was stirred at room temperature for 3 hours. The obtained solid was collected by filtration and washed with ethanol (83.0 kg). The solid was dried under reduced pressure at 60° C. to give 14.0 kg of solid. A mixture of the obtained solid and water (490 kg) was stirred for 35 minutes. The solid was filtered and washed with water (70 L). To the filtrate was added isopropyl acetate (122.2 kg) and 8 M aqueous sodium hydroxide solution (7.0 kg) at room temperature, and the mixture was stirred. The organic layer was separated, warmed to 40° C., and then added a solution of D-(−)-tartaric acid (4.85 kg) in ethanol (27.7 kg). Heptane (71.8 kg) was added and the mixture was stirred at 40° C. for 3 hours and at room temperature for 61 hours. The obtained solid was collected by filtration and washed with isopropyl acetate/heptane/ethanol (4/2/1, 79.1 kg). The reaction mixture was dried under reduced pressure at 60° C., whereby 9.5 kg of solid was obtained. 9.3 kg of the obtained solid and ethanol (82.5 kg) were dissolved by warming at 70° C. At the same temperature, heptane (122.0 kg) was added and aged for 8 hours at around 60° C., and then cooled to 20° C. over 13 hours. The obtained solid was collected by filtration and washed with heptane/ethanol (3/1, 26.4 kg). The drying under reduced pressure at 60° C. gave the title compound (6.0 kg, >99.9% ee).

Example 3

(S)-6-chloro-4-(1-methoxyethyl)-1,5-naphthyridine-3-amine

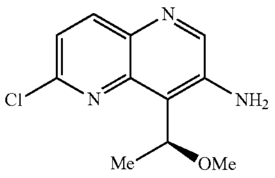 [SMILES: CO[C@@H](C)c1c(N)cnc2ccc(Cl)nc12]

To a solution of (S)-6-chloro-4-(1-hydroxyethyl)-1,5-naphthyridine-3-amine (3.27 g) in THF (33 mL) was added 60% sodium hydride (613.8 mg) at 0° C., and the mixture was stirred at the same temperature for 30 minutes. Methyl iodide (2.39 g) was added to the reaction mixture at 0° C., and the mixture was stirred at room temperature for 2 hours. The reaction mixture was added to ice water and extracted with ethyl acetate. The organic layer was washed with saturated brine, dried over sodium sulfate, and concentrated under reduced pressure. The obtained residue was dissolved in methyl tert-butyl ether at 50° C., and then hexane was added at the same temperature, and the mixture was stirred for 1 hour. The reaction mixture was further stirred at room temperature overnight, and the obtained solid was collected by filtration and washed with hexane to give the title compound (1.69 g, 99.9% ee).

MS: $[M+H]^+$ 238.0

Example 4

(S)-6-chloro-4-(1-methoxyethyl)-1,5-naphthyridine-3-amine

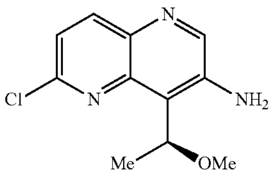 [SMILES: CO[C@@H](C)c1c(N)cnc2ccc(Cl)nc12]

(1) A mixture of (S)-6-chloro-4-(1-hydroxyethyl)-1,5-naphthyridine-3-amine hemi (D)-(−)-tartrate (1.0 g) and acetonitrile (20 mL) was cooled to 5° C., and sodium tert-butoxide (965.2 mg) was added. 10 minutes later, methyl p-toluenesulfonate (0.507 mL) was added to the mixture, and the mixture was stirred for 3 hours. Sodium tert-butoxide (64.3 mg) was added, and the mixture was stirred for 1 hour. Water (5 mL) was added to the reaction mixture, and the mixture was concentrated under reduced pressure to 10 mL. Water (15 mL) was added to the reaction mixture. The obtained suspension was stirred at room temperature, and the solid was filtered. The obtained solid was washed with water (5 mL) and dried under reduced pressure at 60° C. to give the title compound (584.8 mg).

$^1H$ NMR (500 MHz, DMSO-$d_6$) δ 1.42 (3H, d, J=6.94 Hz), 3.21 (3H, s), 5.62 (1H, d, J=6.62 Hz), 6.20 (2H, s), 7.38 (1H, d, J=8.51 Hz), 8.18 (1H, d, J=8.51 Hz), 8.56 (1H, s).

(2) A mixture of (S)-6-chloro-4-(1-hydroxyethyl)-1,5-naphthyridine-3-amine hemi-(D)-(−)-tartrate (5.8 kg), acetonitrile (91.0 kg) and DMF (27.4 kg) was heated at 50° C. and stirred for 50 minutes. The reaction mixture was cooled to 5° C., and sodium tert-butoxide (4.7 kg) was added to the mixture, followed by the addition of methyl p-toluenesulfonate (3.7 kg), and the mixture was stirred for 4 hours. Sodium tert-butoxide (0.2 kg) was added, and the mixture was stirred for 2 hours. The mixture was warmed to 25° C. and stirred for 2 hours, and then water (29.0 kg) was added. The mixture was concentrated under reduced pressure to 30 L, and then water (128 kg) was added. The pH was adjusted to 5 with 6 M aqueous hydrochloric acid solution. The mixture was stirred for 4 hours, and the solid was collected by filtration. The obtained solid was washed with water (58 kg) and dried under reduced pressure at 60° C. to give the title compound (3.68 kg).

Example 5

(S)—N-(6-chloro-4-(1-methoxyethyl)-1,5-naphthyridine-3-yl)-N'-(6-(2H-1, 2, 3-triazole-2-yl)-5-(trifluoromethyl) pyridine-3-yl)urea

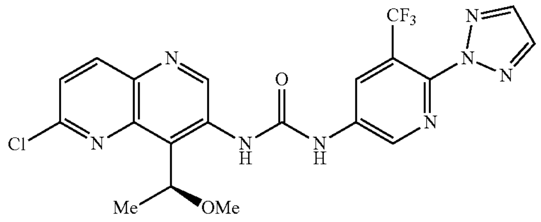 [SMILES: CO[C@@H](C)c1c(NC(=O)Nc2cnc(-n3nccn3)c(C(F)(F)F)c2)cnc2ccc(Cl)nc12]

To a solution of triphosgene (17.48 g) in THF (280 mL) was added (S)-6-chloro-4-(1-methoxyethyl)-1,5-naphthyridine-3-amine (28 g) and DIEA (61.56 mL) at 0° C., and the reaction mixture was stirred at the same temperature for 1 hour. To the reaction mixture was added 6-(2H-1,2,3-triazole-2-yl)-5-(trifluoromethyl)pyridine-3-amine (29.7 g) at 0° C., and the reaction mixture was stirred at room temperature overnight. The reaction mixture was added to water, and the aqueous layer was extracted with ethyl acetate/THF. The organic layer was washed with water and then saturated brine, dried over anhydrous magnesium sulfate, and the solvent was evaporated under reduced pressure. The residue was dissolved in ethyl acetate at 70° C., and the insoluble substance was filtered through Celite. To the filtrate was added NH silica gel, and the mixture was stirred at 70° C. for 1 hour. The insoluble residue was filtered and concentrated under reduced pressure. The residue was dissolved in ethyl acetate at 70° C., and n-heptane was added dropwise to the mixed solution at the same temperature. The mixed solution was stirred at the same temperature for 1 hour, cooled to room temperature, and stirred at the same temperature overnight. The precipitate was collected by filtration and washed with n-heptane to give the title compound (41.3 g, 99.5% ee).

$^1H$ NMR (300 MHz, DMSO-$d_6$) δ 1.56 (3H, d, J=6.8 Hz), 3.36 (3H, s), 5.75-5.94 (1H, m), 7.77 (1H, d, J=8.7 Hz), 8.18 (2H, s), 8.46 (1H, d, J=8.7 Hz), 8.74 (1H, d, J=2.6 Hz), 8.89 (1H, d, J=2.3 Hz), 9.24 (1H, s), 9.69 (1H, s), 10.89 (1H, br s). MS: $[M+H]^+$ 493.2

Example 6

(S)—N-(6-chloro-4-(1-methoxyethyl)-1,5-naphthyridine-3-yl)-N'-(6-(2H-1,2,3-triazole-2-yl)-5-(trifluoromethyl) pyridine-3-yl)urea

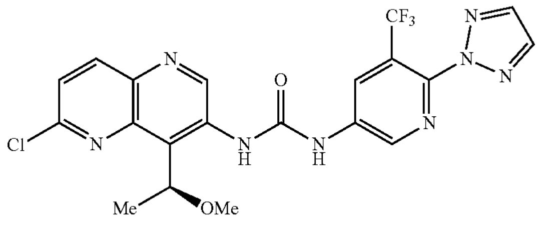 [SMILES: CO[C@@H](C)c1c(NC(=O)Nc2cnc(-n3nccn3)c(C(F)(F)F)c2)cnc2ccc(Cl)nc12]

(1) Under nitrogen atmosphere, (S)-6-chloro-4-(1-methoxyethyl)-1,5-naphthyridine-3-amine (3.00 g) and phenyl 6-(2H-1,2,3-triazole-2-yl)-5-(trifluoromethyl)pyridine-3-aminocarbamate (5.29 g) were dissolved in DMF (15 mL) at 100° C., and the obtained mixture was stirred at the same temperature for 4 hours. The mixture was cooled to room temperature, and ethanol (9 mL) and water (51 mL) were added. The obtained suspension was stirred at room temperature for 2 hours.

The obtained solid was collected by filtration, washed with ethanol/water (1/1, 15 mL), dried under nitrogen. The obtained solid was dissolved in ethyl acetate (45 mL) at 70° C. The insoluble residue was filtered at the same temperature, and the filtrate was concentrated to 21 mL. The residue was warmed to 70° C., added heptane (60 mL), and the mixture was stirred at 5° C. for 2 hours. The obtained solid was collected by filtration and washed with ethyl acetate/heptane (1/1, 24 mL). The solid was dried under reduced pressure at 60° C. to give the title compound (4.63 g, 99.1% ee).

$^1H$ NMR (500 MHz, DMSO-$d_6$) δ 1.57 (3H, d, J=6.62 Hz), 3.38 (3H, s), 5.86 (1H, q, J=6.62 Hz), 7.76 (1H, d, J=8.83 Hz), 8.20 (2H, s), 8.45 (1H, d, J=8.83 Hz), 8.75 (1H, s), 8.90 (1H, s), 9.26 (1H, s), 9.70 (1H, s), 10.91 (1H, br s). $^{13}C$ NMR (126 MHz, DMSO-$d_6$) δ 19.76, 57.28, 73.66, 120.91, 121.17, 121.47, 123.64, 124.78, 125.40, 125.45, 131.89, 134.43, 136.94, 138.17, 138.64, 141.19, 141.60, 141.65, 142.10, 148.05, 150.37, 152.60.

(2) Under nitrogen atmosphere, (S)-6-chloro-4-(1-methoxyethyl)-1,5-naphthyridine-3-amine (3.6 kg) and phenyl 6-(2H-1,2,3-triazole-2-yl)-5-(trifluoromethyl)pyridine-3-aminocarbamate (6.6 kg) were dissolved in DMF (17.0 kg) at 100° C., and the obtained mixture was stirred at the same temperature for 9 hours and 20 minutes. The mixture was cooled to room temperature, and ethanol (8.5 kg) and water (61.0 kg) were added. The obtained suspension was stirred at room temperature for 3 hours and 20 minutes. The obtained solid was collected by filtration, washed with ethanol/water (1/1, 14.1 kg), and dried under reduced pressure at 60° C. The obtained solid (7.6 kg) was added to ethyl acetate (48.0 kg), and the mixture was stirred at 70° C. for 3 hours. The insoluble residue was filtered at the same temperature and washed with ethyl acetate (180.0 kg). The filtrate was concentrated under reduced pressure to 72 L. The mixture was warmed to 70° C., added heptane (72.0 kg), and stirred at the same temperature for 1 hour. The mixture was cooled to 5° C. and stirred for 5 hours. The obtained solid was collected by filtration and washed with ethyl acetate/heptane (1/1, 24.0 kg). The solid was dried under reduced pressure at 60° C. to give the title compound (4.20 kg). To ethyl acetate (32.2 kg) was added the obtained solid (4.1 kg), and the mixture was stirred at 70° C. for 15 minutes. The insoluble residue was filtered at the same temperature and washed with ethyl acetate (8.0 kg). The filtrate was warmed to 70° C., add heptane (47.0 kg), and stir at the same temperature for 1 hour. The mixture was cooled to 5° C. and stirred for 5 hours. The obtained solid was collected by filtration and washed with ethyl acetate/heptane (1/1, 13.0 kg). The solid was dried under reduced pressure at 60° C. to give the title compound (3.32 kg, >99.9% ee).

[MALT1 Inhibitory Activity of Compound (X), Etc.]

Test Example 1

(1) Preparation of Recombinant Human MALT1 Protein

On the human MALT1 gene, PCR was carried out using GC-030-D09 (pENTR221/MALT1, GeneCopoeia) as a template with primers having BamH I restriction enzyme at the N-terminal and Not I restriction enzyme at the C-terminal to form a human MALT1 (340-789aa) dimer. On the leucine zipper gene of yeast GCN4, PCR was carried out using yeast DNA as a template with primers having Nde I restriction enzyme at the N-terminal, and a linker sequence (GGAAGTGGCTCAGGTAGC (SEQ ID NO: 1)) and BamH I restriction enzyme at the C-terminal to yield yeast GCN4 (251-281aa). Both of the obtained fragments were treated with the restriction enzymes, and inserted between Nde I and Not I of a pET28a (Novagen) vector to yield a recombinant human MALT1 protein expression vector pET28a/His-LZ-hMALT1v1 (340-789)-His.

The recombinant human MALT1 protein was prepared by transforming the expression plasmid prepared as above with ECOS Competent *E. coli* BL21 (DE3) (Nippon Gene Co., Ltd.). *Escherichia coli* obtained by transformation was inoculated into 300 mL of LB medium (1% tryptone, 0.5% yeast extract, 0.5% sodium chloride, 0.01% ampicillin) and cultured at 30° C. for 16 hours. The obtained culture solution was transplanted into a jar culture tank containing 6 L of a main fermentation medium (0.3% potassium dihydrogen phosphate, 0.6% disodium hydrogen phosphate, 0.1% ammonium chloride, 0.05% sodium chloride, 0.024% magnesium sulfate, 0.01% Antifoam PE-L, 1.5% sorbitol, 1.5% casamino acid, 0.5% yeast extract and 0.01% ampicillin), and the culturing was started at 37° C., aeration rate of 5 L/min, and stirring rotation speed of 400 rpm. When the turbidity of the culture solution reached about 500 Klett units, the culture temperature was lowered to 16° C., and then isopropyl-β-D-thiogalactopyranoside (IPTG) was added to a final concentration of 0.1 mM. Furthermore, culturing was carried out for 16 hours to induce expression of human MALT1 protein. After completion of the culture, the culture solution was centrifuged at 5,000 rpm for 10 minutes. After suspending the obtained human MALT1 protein-expressing *Escherichia coli* in a buffer solution containing 50 mM Tris-HCl pH 8.0, 300 mM NaCl, 5 mM DTT, 5 U/ml benzonase, 20 mM imidazole, 10% glycerol and 0.1% NP-40, sonication was carried out using Sonifier (Branson). This crushed liquid was centrifuged (15,300×G, 30 min, TOMY MX-301), and the obtained supernatant was passed through and adsorbed to a Ni-NTA Superflow (QIAGEN) column previously equilibrated with 50 mM Tris-HCl pH 8.0, 300 mM NaCl, 5 mM DTT and 10% glycerol, followed by elution in a buffer containing 50 mM Tris-HCl pH 8.0, 300 mM NaCl, 5 mM DTT, 10% glycerol and 250 mM imidazole. Furthermore, gel filtration was carried out on a Superdex 200 pg column previously equilibrated with a buffer solution containing 50 mM Tris-HCl pH 8.0, 150 mM NaCl, 5 mM DTT and 10% glycerol to collect a target fraction, and equal amounts of 50 mM Tris-HCl pH 8.0, 150 mM NaCl, 5 mM DTT and 90% glycerol were added to yield purified human MALT1 protein. The prepared protein was stored at −30° C., and the protein concentration was measured with a BCA Protein Assay Kit (PIERCE) using BSA as a standard.

(2) Measurement of MALT1 Enzyme Inhibitory Activity

To a 384 well black plate (Greiner) was added 2 μL of a compound solution diluted with an assay buffer ((20 mM HEPES (Dojin Laboratories), 10 mM KCl (Wako Pure Chemical Industries, Ltd.), 1.5 mM $MgCl_2$ (Sigma-Aldrich), 1 mM EDTA (pH 8.0) (Nippon Gene Co., Ltd.), 0.01% Triton X-100 (Sigma-Aldrich) and 1 mM DTT (Wako Pure Chemical Industries, Ltd.)). Subsequently, 2 μL of a purified recombinant human MALT1 enzyme solution was added, followed by incubation for 60 minutes at room temperature. To the mixture were added 2 μL of a substrate solution (75 μM Ac-LRSR-AFC (SM Biochemicals), 20 mM HEPES (Dojin Laboratories), 10 mM KCl (Wako Pure Chemical Industries, Ltd.), 1.5 mM $MgCl_2$ (Sigma-Aldrich), 1 mM EDTA (pH 8.0) (Nippon Gene Co., Ltd.), 0.01% Triton X-100 (Sigma-Aldrich) and 1 mM DTT (Wako Pure Chemical Industries, Ltd.), followed by incubation for 60 minutes at room temperature. The fluorescence values of excitation 400 nm and emission 485 nm immediately after substrate addition and after enzymatic reaction were measured with a plate reader Envision (PerkinElmer), and the fluorescence values increased by enzymatic reaction were used for calculation of the inhibition rate (%). The inhibition rate (%) was calculated regarding the value without enzyme addition as 100% and the value without compound addition as 0%.

The measurement results of MALT1 enzyme inhibitory activity are shown below.

TABLE 1

| Compound | MALT1 enzyme inhibition rate (%) at 3 μM compound |
|---|---|
| X1 | 99 |
| X2 | 101 |

From these results, it has been indicated that the compound (X) has MALT1 enzyme inhibitory activity.

Test Example 2

Measurement of Growth Inhibitory Activity Using OCI-Ly3 Cells

OCI-Ly3 cells were seeded in a cell culture medium IMDM (Fujifilm Wako Pure Chemical Corporation) containing 20% FCS (fetal calf serum, Thermo Fisher Scientific) and monothioglycerol (Fujifilm Wako Pure Chemical Corporation) so as to be at 1.25×103 cells/well on a 96-well plate. Cell Titer-Glo solution (Promega) was added to cells to which the test compound had not been added, followed by stirring at room temperature for 15 minutes. Subsequently, the luminescence value was measured with Envision (PerkinElmer) on the day of seeding. Cells to which the test compound dissolved in dimethyl sulfoxide (Fujifilm Wako Pure Chemical Corporation) had been added were allowed to stand in a CO2 incubator (37° C.) for 6 days. Subsequently, the luminescence value was measured in the same manner. The inhibition rate (%) of the test compound on OCI-Ly3 cell growth was calculated by the following formula.

Cell growth inhibition rate (%)=(1−(Luminescent value on day 6 of test compound treatment−Luminescent value before test compound treatment)/(Luminescent value on day 6 without compound addition−Luminescent value before compound treatment))×100

The measurement results of the cell growth inhibition rate are shown below.

TABLE 2

| Compound | Cell growth inhibition rate (%) at 3 μM compound |
|---|---|
| X1 | 97 |
| X2 | 99 |

From these results, it has been indicated that the compound (X) inhibits cell growth.

Test Example 3

Antitumor Effect on OCI-Ly3 Cell-Bearing Cancer Model

Human diffuse large-cell B-cell lymphoma cells OCI-Ly3 (DSMZ, German Collection of Microorganisms and Cell Cultures) were suspended in a Matrigel (BD Biosciences): HBSS (Thermo Fisher Scientific)=1:1 solution, and 1×107 cells were transplanted subcutaneously into the abdomen of NOG female mice (CLEA Japan, Inc.). The tumor diameter of the engrafted tumor was measured, and the tumor volume was calculated by the following formula.

Tumor volume=major axis×minor axis×minor axis×(1/2)

Individuals with the engrafted tumor having a tumor volume of about 120 $mm^3$ were selected, and 6 animals per group were used in the experiment. A suspension of the test compound in 0.5% methylcellulose solution (Fujifilm Wako Pure Chemical Corporation) was orally administered at a dose of 10 mg/kg (10 mL/kg) twice daily for 3 weeks. The tumor volume was measured on the day before the start of administration and every 3 to 4 days over time, and the tumor diameter was finally measured the day after the end of administration for 21 days to calculate the tumor volume. The tumor growth of the test compound-administered group compared with the control-administered group was calculated by the following formula as an average tumor volume increase ratio T/C.

*T/C*=((Tumor volume after the end of administration for the test compound-administered group−Tumor volume of the day before the start of administration for the test compound-administered group)/(Tumor volume after the end of administration for the control-administered group−Tumor volume of the day before the start of administration for the control-administered group))×100

The T/C of the test compound is shown below.

TABLE 3

| Compound | Dose (mg/kg) | T/C (%) |
|---|---|---|
| X1 | 10 | 2.0 |
| X2 | 10 | 38.7 |

From these results, it has been indicated that the compound (X) has an antitumor effect in human diffuse large-cell B-cell lymphoma cell OCI-Ly3-subcutaneously transplanted models.

INDUSTRIAL APPLICABILITY

The present invention provides an industrial production method for efficiently synthesizing a compound (X) or a salt thereof, which is a novel MALT1 inhibitor having a high optical purity, in a large amount with a shorter number of steps, without the need for complicated operations such as chiral column purification, and is useful in the pharmaceutical industry.

This application is based on Japanese Patent Application No. 2020-092687 (application date 27 May 2020) filed in Japan, the content of which is incorporated herein by reference in its entirety.

The invention claimed is:

1. A method for producing a compound of the formula (B-2):

(B-2)

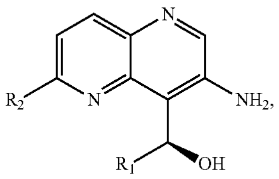

wherein $R_1$ represents a methyl group and $R_2$ represents a $C_{1-6}$ alkyl group or a halogen atom, or a salt thereof, comprising crystallizing a salt of a compound of the formula (B-1):

(B-1)

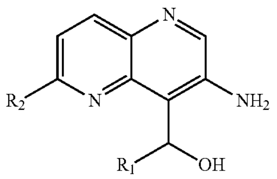

and an optically active organic acid.

2. A method for producing a compound of the formula (C):

(C)

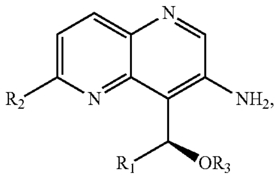

wherein $R_1$ represents a methyl group, $R_2$ represents a $C_{1-6}$ alkyl group or a halogen atom and $R_3$ represents a $C_{1-6}$ alkyl group, or a salt thereof, comprising 1) crystallizing a salt of the compound of the formula (B-1):

(B-1)

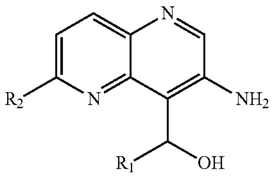

and an optically active organic acid to obtain a compound of the formula (B-2):

(B-2)

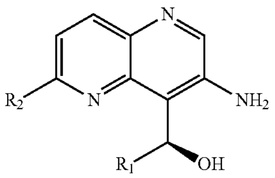

or a salt thereof, and 2) subjecting the obtained compound (B-2) or a salt thereof to an alkylation reaction.

3. A method for producing a compound of the formula (X):

(X)

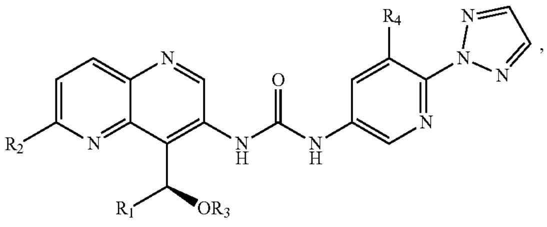

wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted with halogen atoms, or a salt thereof, comprising 1) crystallizing a salt of a compound of the formula (B-1):

(B-1)

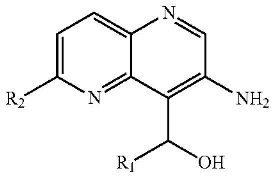

and an optically active organic acid to obtain a compound of the formula (B-2):

(B-2)

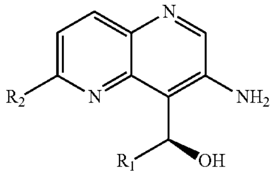

or a salt thereof, 2) subjecting the obtained compound (B-2) or a salt thereof to an alkylation reaction to obtain the compound of the formula (C):

(C)

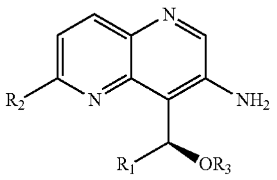

or a salt thereof, and 3) subjecting the obtained compound (C) or a salt thereof to a reaction with compound of the formula (D):

(D)

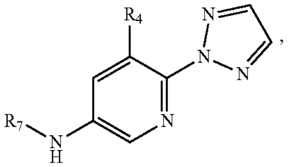

wherein $R_7$ represents a hydrogen atom, a $C_{1-6}$ alkoxy group which may be substituted with halogen atoms, or an aryloxycarbonyl group which may be substituted with nitro groups or a salt thereof.

4. A method for producing a compound of the formula (B-2):

(B-2)

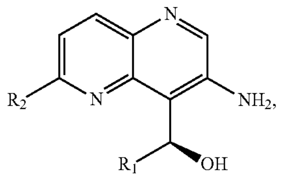

wherein $R_1$ represents a methyl group and $R_2$ represents a $C_{1-6}$ alkyl group or a halogen atom, or a salt thereof, comprising 1) subjecting the compound of the formula (A):

(A)

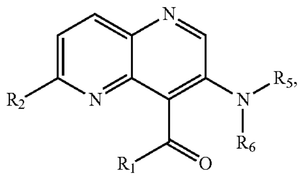

wherein $R_5$ and $R_6$ independently represent a hydrogen atom or an amino protecting group, or a salt thereof 1) to an asymmetric reduction reaction of a carbonyl group, or 2) to an asymmetric reduction reaction of a carbonyl group and a deprotection reaction of an amino protecting group to obtain the compound of the formula (B-1):

(B-1)

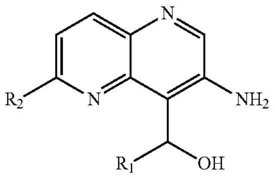

or a salt thereof, and 2) crystallizing a salt of the obtained compound (B-1) and an optically active organic acid.

5. A method for producing a compound of the formula (X):

(X)

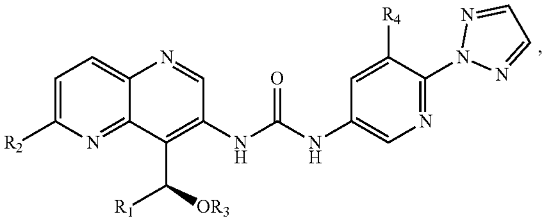

wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted with halogen atoms, or a salt thereof, comprising 1) subjecting the compound of the formula (A):

(A)

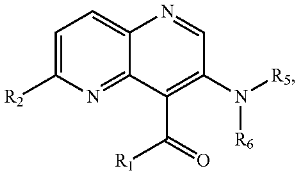

wherein $R_5$ and $R_6$ independently represent a hydrogen atom or an amino protecting group, or a salt thereof 1) to an asymmetric reduction reaction of carbonyl group, or 2) to an asymmetric reduction reaction of carbonyl group and a deprotection reaction of an amino protecting group to obtain the compound of the formula (B-1):

(B-1)

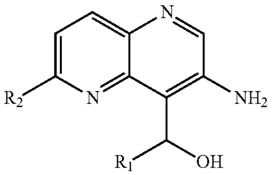

or a salt thereof, 2) crystallizing a salt of the obtained compound (B-1) and an optically active organic acid to obtain the compound of the formula (B-2):

(B-2)

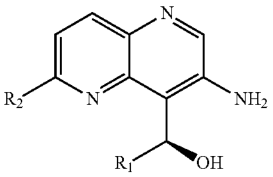

or a salt thereof, 3) subjecting the obtained compound (B-2) or a salt thereof to an alkylation reaction to obtain the compound of the formula (C):

(C)

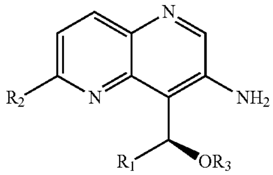

or a salt thereof, and 4) subjecting the obtained compound (C) or a salt thereof to a reaction with compound of the formula (D):

(D)

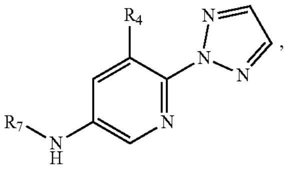

wherein $R_7$ represents a hydrogen atom, a $C_{1-6}$ alkoxy group which may be substituted with halogen atoms, or an aryloxycarbonyl group which may be substituted with nitro groups, or a salt thereof.

6. The method for producing the compound of the formula (B-2) according to claim 1, wherein the optically active organic acid is selected from D-(−)-tartaric acid, L-(+)-tartaric acid, (S)-(−)-2-pyridone-5-carboxylic acid, (R)-(+)-2-pyridone-5-carboxylic acid, L-malic acid, D-malic acid, (S)-(+)-camphor-10-sulfonic acid, (R)-(−)-camphor-10-sulfonic acid, (S)-(+)-2-(6-methoxy-2-naphthyl) propionic acid, (R)-(−)-2-(6-methoxy-2-naphthyl) propionic acid, (+)-cis-2-benzamidocyclohexanecarboxylic acid, (−)-cis-2-benzamidocyclohexanecarboxylic acid, dehydroabietic acid, (R)-(−)-N-(3,5-dinitrobenzoyl)-α-phenylglycine, (S)-(+)-N-(3,5-dinitrobenzoyl)-α-phenylglycine, D-(−)-quinic acid and L-(+)-quinic acid.

7. The method for producing the compound of the formula (B-2) according to claim 1, wherein the optically active organic acid is D-(−)-tartaric acid.

8. A method for producing a compound of the formula (X):

(X)

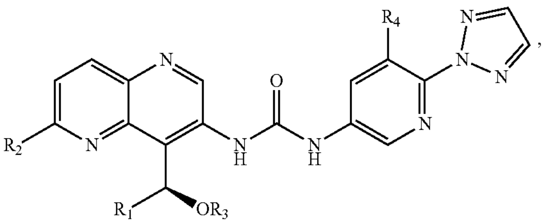

wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted with halogen atoms, or a salt thereof comprising, subjecting the compound of the formula (C):

(C)

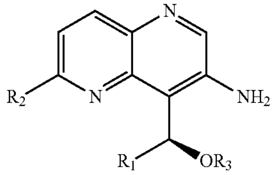

or a salt thereof to a reaction with compound of the formula (D):

(D)

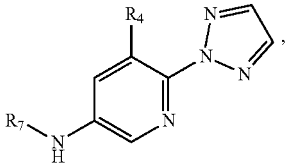

wherein $R_7$ represents a hydrogen atom, a $C_{1-6}$ alkoxy group which may be substituted with halogen atoms, or an aryloxycarbonyl group which may be substituted with nitro groups, or a salt thereof.

9. A method for producing a compound of the formula (X):

(X)

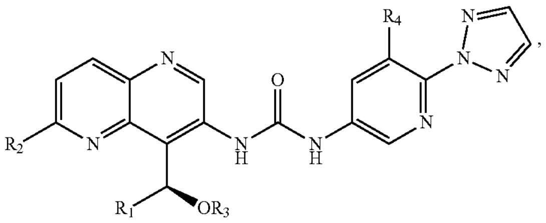

wherein $R_1$ represents a methyl group, $R_2$ represents a $C_{1-6}$ alkyl group or a halogen atom, $R_3$ represents a $C_{1-6}$ alkyl group and $R_4$ represents a $C_{1-6}$ alkyl group which may be substituted with halogen atoms, or a salt thereof comprising, 1) subjecting compound of the formula (B-2):

(B-2)

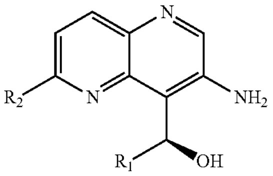

or a salt thereof to an alkylation reaction to obtain the compound of the formula (C):

(C)

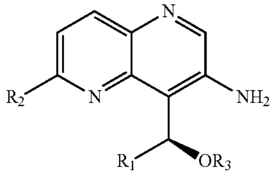

or a salt thereof, and 2) subjecting the obtained compound (C) or a salt thereof to a reaction with compound of the formula (D):

(D)

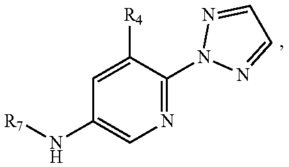

wherein $R_7$ represents a hydrogen atom, a $C_{1-6}$ alkoxy group which may be substituted with halogen atoms, or an aryloxycarbonyl group which may be substituted with nitro groups, or a salt thereof.

10. A compound of the formula (B-2):

(B-2)

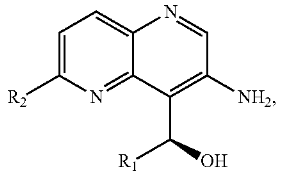

wherein the compound of the formula (B-2) is (S)-6-chloro-4-(1-hydroxyethyl)-1,5-naphthyridine-3-amine hemi-D-(−)-tartrate.

* * * * *